United States Patent
Milbrandt et al.

(10) Patent No.: US 12,390,482 B2
(45) Date of Patent: Aug. 19, 2025

(54) NEUROLYTIC AGENTS AND METHODS OF USING AND IDENTIFYING SAME

(71) Applicant: Washington University, St. Louis, MO (US)

(72) Inventors: Jeffrey Milbrandt, St. Louis, MO (US); Aaron DiAntonio, St. Louis, MO (US); Tong Wu, St. Louis, MO (US); Amy Strickland, St. Louis, MO (US); Adam Bloom, St. Louis, MO (US); Yo Sasaki, St. Louis, MO (US); Jian Zhu, St. Louis, MO (US); Yurie Yamada, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 17/851,954

(22) Filed: Jun. 28, 2022

(65) Prior Publication Data

US 2022/0409648 A1    Dec. 29, 2022

Related U.S. Application Data

(60) Provisional application No. 63/215,682, filed on Jun. 28, 2021.

(51) Int. Cl.
*A61K 31/706* (2006.01)
*A61K 31/4402* (2006.01)

(52) U.S. Cl.
CPC ........ *A61K 31/706* (2013.01); *A61K 31/4402* (2013.01)

(58) Field of Classification Search
CPC .................................................. A61K 31/706
See application file for complete search history.

(56) References Cited

PUBLICATIONS

Loreto et al., "Potent activation of SARM1 by VMN underlies vacor neurotoxicity", BioRxiv, Jun. 23, 2021 (Year: 2021).*
Berta T, Qadri Y, Tan PH, Ji RR. Targeting dorsal root ganglia and primary sensory neurons for the treatment of chronic pain. Expert Opin Ther Targets. Epub May 16, 2017 (Year: 2017).*
Elliot Krames, "The Role of the Dorsal Root Ganglion in the Development of Neuropathic Pain", Pain Medicine, Oct. 2014 (Year: 2014).*
Frode et al., "Animal models to test drugs with potential antidiabetic activity", ScienceDirect, Nov. 4, 2007 (Year: 2007).*
Watson et al., "Vacor Neuropathy: Ultrastructural and Axonal Transport Studies", Journal of Neuropathology and Experimental Neurology (1987)) (Year: 1987).*
Buonvicino et al., "Identification of the Nicotinamide Salvage Pathway as a New Toxification Route for Antimetabolites", Cell Chemical Biology, Apr. 19, 2018 (Year: 2018).*
Coleman Laboratory, "Vacor: The Former Rat Poison Now Driving Drug Discovery for Axonal Disorders (For School and College Students)," University of Cambridge Blog, 2024, 5 pages, Retrieved from the Internet: URL: https://colemanlab.brc.cam.ac.uk/blog/vacor-former-rat-poison-now-driving-drug-discovery-axonal-disorders-school-and-college-students.
Wecker L., et al., "3-Acetylpyridine Neurotoxicity in Mice," Neurotoxicology, Jan. 2017, vol. 58, pp. 143-152.

* cited by examiner

*Primary Examiner* — Brandon J Fetterolf
*Assistant Examiner* — Gillian A Hutter
(74) *Attorney, Agent, or Firm* — Polsinelli PC

(57) ABSTRACT

Among the various aspects of the present disclosure is the provision is the provision of a SARM1 activating agent or prodrug thereof and methods of using same.

13 Claims, 16 Drawing Sheets

(13 of 16 Drawing Sheet(s) Filed in Color)

NEUROLYTIC AGENTS AND METHODS OF USING AND IDENTIFYING SAME

CROSS REFERENCE TO RELATED APPLICATIONS

This application claims the benefit of U.S. Provisional Application 63/215,682, filed Jun. 28, 2021 the disclosure of which is hereby incorporated by reference in its entirety.

GOVERNMENT SUPPORT

This invention was made with government support under NS087632, NS119812, NS065053, and AG013730 awarded by the National Institutes of Health. The government has certain rights in the invention.

FIELD OF THE TECHNOLOGY

This disclosure generally relates to methods, compositions, kits, and agents useful for activating SARM1 to promote targeted neurolysis.

BACKGROUND

Axon degeneration is an essential feature of many neurodegenerative conditions. SARM1 is the central executioner of pathological axon degeneration, and a promising therapeutic target for a wide range of neurological disorders. SARM1 also promotes neuronal cell death in response to oxygen-glucose deprivation, viral infection, and mitochondrial toxins. SARM1 is comprised of an autoinhibitory N-terminal ARM domain, tandem SAM domains that mediate octamerization, and a C-terminal TIR domain. This TIR domain is the original exemplar of a large family of TIR domain $NAD^+$ hydrolases, conserved throughout all domains of life from bacteria and archaea to plants and animals. In healthy neurons, SARM1 is maintained in an autoinhibited state via multiple intra- and intermolecular interactions, including binding of the N-terminal ARM domain to the C-terminal TIR-domain. SARM1 autoinhibition is regulated by an allosteric binding site within the autoinhibitory ARM domain that can bind either nicotinamide adenine dinucleotide ($NAD^+$) or its precursor, nicotinamide mononucleotide (NMN). Axon injury leads to loss of the $NAD^+$ biosynthetic 84111356.1 enzyme NMNAT2, resulting in an increased NMN/$NAD^+$ ratio that favors NMN binding to the allosteric site. The switch from $NAD^+$ to NMN binding induces compaction of the autoinhibitory ARM domain and permits the formation of TIR-TIR interactions that activate the enzyme.

Neural ablation is a procedure in which a portion of nerve tissue is damaged, destroyed or removed to interrupt normal signaling pathways. Traditionally, ablation processes have been used to treat pain or to control arrhythmias in patients with heart disease. Currently, the chemical agents used to produce therapeutic neurolysis, phenol and ethanol, are not neuro-specific, damage adjacent tissues, and can cause systemic side-effects.

Thus, there is a need in the art compositions and methods which provide specific neurolytic agents.

SUMMARY

Among the various aspects of the present disclosure is the provision of a SARM1 activating agent or prodrug thereof and methods of using same.

An aspect of the present disclosure provides for a method of activating SARM1 in a subject in need thereof. In some embodiments, the method comprises administering an amount of a SARM1 activating neurolytic agent effective to initiate, trigger, or promote axon degeneration, degeneration of sensory pain fibers, motor fibers, local degeneration of nerves (e.g., sensory or motor), neurolysis, or Wallerian degeneration. In some embodiments, the SARM1 activating neurolytic agent does not cause substantial systemic effects. In some embodiments, the subject has or is suspected of having a disease, disorder, or condition where degeneration of sensory neurons is therapeutic. In some embodiments, the subject has or is suspected of having a disease, disorder, or condition where degeneration of motor neurons is therapeutic.

In some embodiments, the subject has or is suspected of having a pain condition. In some embodiments, the pain condition is post-amputation pain, post-injury pain, post-surgical pain, post-traumatic pain, or neuropathic pain. In some embodiments, the pain condition is neuroma pain. In some embodiments, the subject has or is suspected of having neuroma, an inappropriate growth of sensory axons after injury or surgery. In some embodiments, the SARM1 activators applied to neuromas selectively trigger their degeneration and is more effective than surgical removal. In some embodiments, the subject has or is suspected of having a motor disease disorder, or condition.

In some embodiments, the subject has or is suspected of having a muscle contraction disease, disorder, or condition. In some embodiments, the motor disease disorder, or condition is a muscle contraction disease, disorder, or condition. In some embodiments, the motor disease disorder, or condition or muscle contraction disease disorder, or condition is selected from one or more of: neck spasms (cervical dystonia), excessive sweating (hyperhidrosis), an overactive bladder, lazy eye, facial wrinkles, migraines, muscle contractures, cerebral palsy, bladder dysfunction, or eye twitching. In some embodiments, the subject has or is suspected of having a cosmetic defect, facial paralysis, facial palsy (e.g., Bells), synkinesis, hypertonicity of the buccinator muscle, hemifacial spasm, facial wrinkles, neck spasms (cervical dystonia), excessive sweating (hyperhidrosis), an overactive bladder, lazy eye, eye twitching, or chronic migraines.

In some embodiments, the SARM1 activation agent: binds the SARM1 allosteric pocket and activates SARM1; is an agent that contains a pyridine ring and that is a substrate for nicotinamide phosphoribosyl transferase (NAMPT) enzyme, resulting in a mononucleotide compound (compound-MN); and/or the compound-MN binds the allosteric pocket of SARM1 and activates the SARM1 NADase. In some embodiments, compound-MN is not a substrate for the next enzyme in the pathway, nicotinamide mononucleotide adenyltransferase (NMNAT), such that variants of $NAD^+$ are not substantially formed that might have off-target effects. In some embodiments, the SARM1 activation neurolytic agent is capable of being converted by NAMPT to a pyridine-SARM1-activating mononucleotide. In some embodiments, the SARM1 activation neurolytic agent is metabolized intracellularly to generate a SARM1 active metabolite. In some embodiments, the SARM1 activation neurolytic agent is selected from: 3-acetylpyridine mononucleotide (3-APMN); 2-acetylpyridine mononucleotide (2-APMN); Vacor-mononucleotide (VMN); or prodrug thereof.

In some embodiments, the SARM1 activation neurolytic agent is a class of pyridine-derivatives that directly activates SARM1. In some embodiments, the SARM1 activation neurolytic agent is a pyridine-derivative related to NMN, such as 3-acetylpyridine mononucleotide (3-APMN). In some embodiments, the SARM1 activation neurolytic agent is a cell-permeable parent compound of the SARM1 neurolytic activator, such as 3-acetylpyridine (3-AP), the parent of 3-APMN. In some embodiments, the SARM1 activation neurolytic agent is a pyridine-derivative SARM1 activator, such as 2-aminopyridine mononucleotide, which is generated from its cell-permeable parent compound 2-aminopyridine. In some embodiments, the SARM1 activation neurolytic agent is vacor, which is converted into its mononucleotide, VMN to activate SARM1.

In some embodiments, administering the SARM1 activation neurolytic agent does not substantially damage non-neural tissues adjacent to a targeted nerve (e.g., sensory or motor), such as muscle. In some embodiments, administering the SARM1 activation neurolytic agent does not affect other nerves (e.g., sensory or motor) outside the site of application or cause systemic effects. In some embodiments, administering the SARM1 activation neurolytic agent is neuro-specific, does not damage adjacent or local tissues, and does not can cause systemic side-effects. In some embodiments, administering the SARM1 activation neurolytic agent results in: activating SARM1 and triggers local degeneration of sensory pain fibers; activating SARM1 and triggers local degeneration of motor fibers; and/or narrowly-targeted local degeneration. Another aspect of the present disclosure provides for a pharmaceutical formulation comprising a SARM1 activating neurolytic agent in an ointment (e.g., topical), cream (e.g., topical), or nanoparticle formulation (e.g., for injection).

Another aspect of the present disclosure provides for a SARM1 activating agent identified by screening for or identifying and validating potential SARM1 activators useful for therapeutic neurolysis comprising the steps of: measuring SARM1 activation directly in vitro using a fluorescent SARM1 activity probe; measuring cADPR, a specific biomarker of SARM1 activity; assaying axon degeneration in genetically modified mouse neurons that lack SARM1; and/or assaying for the efficacy of test SARM1 activators in the SARM1 allosteric pocket.

In one aspect, the present disclosure provides a method of activating SARM1 in a subject in need thereof by administering an amount of a SARM1 activating neurolytic agent effective to initiate, trigger, or promote axon degeneration, degeneration of sensory pain fibers, degeneration of motor fibers, targeted local degeneration of nerves, neurolysis, or Wallerian degeneration. The SARM1 activating neurolytic agent does not cause substantial systemic effects and acts locally in a targeted fashion through controlled administration to the specific site of desired neurolysis. In some embodiments, the subject has or is suspected of having a disease, disorder, or condition where degeneration of sensory neurons is therapeutic. In other embodiments, the subject has or is suspected of having a disease, disorder, or condition where degeneration of motor neurons is therapeutic.

In some embodiments, the subject has or is suspected of having a pain condition. In some embodiments, the pain condition is post-amputation pain, post-injury pain, post-surgical pain, post-traumatic pain, or neuropathic pain. In some embodiments, the pain condition is neuroma pain. In some embodiments, the subject has or is suspected of having neuroma, an inappropriate growth of sensory axons after injury or surgery. In some embodiments, the SARM1 activator is applied to neuromas selectively trigger their degeneration and is more effective than surgical removal.

In some embodiments, the subject has or is suspected of having a motor disease disorder, or condition. In some embodiments, the subject has or is suspected of having a muscle contraction disease, disorder, or condition. In some embodiments, the motor disease disorder, or condition is a muscle contraction disease, disorder, or condition. In some embodiments, the motor disease disorder, or condition or muscle contraction disease disorder, or condition is selected from one or more of neck spasms (cervical dystonia), excessive sweating (hyperhidrosis), an overactive bladder, lazy eye, facial wrinkles, migraines, muscle contractures, cerebral palsy, bladder dysfunction, or eye twitching.

In some embodiments, the subject has or is suspected of having a cosmetic defect, facial paralysis, facial palsy (e.g., Bells), synkinesis, hypertonicity of the buccinator muscle, hemifacial spasm, facial wrinkles, neck spasms (cervical dystonia), excessive sweating (hyperhidrosis), an overactive bladder, lazy eye, eye twitching, or chronic migraines.

In some embodiments, the SARM1 activation agent binds the SARM1 allosteric pocket and activates SARM1; is an agent that contains a pyridine ring and that is a substrate for nicotinamide phosphoribosyl transferase (NAMPT) enzyme, resulting in a mononucleotide compound (compound-MN); and/or the compound-MN binds the allosteric pocket of SARM1 and activates the SARM1 NADase. In certain embodiments, the SARM1 activation agent is not a substrate for the next enzyme in the pathway, nicotinamide mononucleotide adenyltransferase (NMNAT), such that variants of $NAD^+$ are not substantially formed that might have off-target effects. In some embodiments, the SARM1 activation neurolytic agent is capable of being converted by NAMPT to a pyridine-SARM1-activating mononucleotide. In some embodiments, the SARM1 activation neurolytic agent is metabolized intracellularly to generate a SARM1 active metabolite. In some embodiments, the SARM1 activation neurolytic agent is selected from: 3-acetylpyridine mononucleotide (3-APMN); 2-acetylpyridine mononucleotide (2-APMN); Vacor-mononucleotide (VMN); or prodrug thereof. In some embodiments, the SARM1 activation neurolytic agent is a class of pyridine-derivatives that directly activates SARM1. In some embodiments, the SARM1 activation neurolytic agent is a pyridine-derivative related to NMN, such as 3-acetylpyridine mononucleotide (3-APMN). In some embodiments, the SARM1 activation neurolytic agent is a cell-permeable parent compound of the SARM1 neurolytic activator, such as 3-acetylpyridine (3-AP), the parent of 3-APMN. In some embodiments, the SARM1 activation neurolytic agent is a pyridine-derivative SARM1 activator, such as 2-aminopyridine mononucleotide, which is generated from its cell-permeable parent compound 2-aminopyridine. In some embodiments, the SARM1 activation neurolytic agent is vacor, which is converted into its mononucleotide, VMN to activate SARM1.

In preferred embodiments, administering the SARM1 activation neurolytic agent does not substantially damage non-neural tissues adjacent to a targeted nerve (e.g., sensory or motor), such as muscle. In certain embodiments, administering the SARM1 activation neurolytic agent does not affect other nerves (e.g., sensory or motor) outside the site of application or cause systemic effects. In certain embodiments, administering the SARM1 activation neurolytic agent is neuro-specific, does not damage adjacent or local tissues, and does not can cause systemic side-effects.

In some embodiments, administering the SARM1 activation neurolytic agent results in activating SARM1 and triggers local degeneration of sensory pain fibers; activating SARM1 and triggers local degeneration of motor fibers; and/or narrowly-targeted local degeneration.

In another aspect the present disclosure provides pharmaceutical formulation comprising a SARM1 activating neurolytic agent in an ointment (e.g., topical), cream (e.g., topical), or nanoparticle formulation (e.g., for injection).

In another aspect the present disclosure provides SARM1 activating agent identified by screening for or identifying and validating potential SARM1 activators useful for therapeutic neurolysis comprising the steps of measuring SARM1 activation directly in vitro using a fluorescent SARM1 activity probe; measuring cADPR, a specific biomarker of SARM1 activity; assaying axon degeneration in genetically modified mouse neurons that lack SARM1; and/or assaying for the efficacy of test SARM1 activators in the SARM1 allosteric pocket.

Other objects and features will be in part apparent and in part pointed out hereinafter.

BRIEF DESCRIPTION OF THE FIGURES

The patent or patent application file contains at least one drawing executed in color. Copies of this patent or patent application publication with color drawing(s) will be provided by the Office upon request and payment of the necessary fee.

FIG. 1A depicts a diagram of nicotinamide (Nam) and 3-AP metabolism by NAMPT and NMNAT. X represents amino (Nam) or methyl (3-AP) group. FIG. 1B shows WT and Sarm1 KO DRGs were treated with 3-AP (300 µM) at DIV7. Representative images of axons from WT and Sarm1 KO cultured DRG neurons at 0, 6, 24, 48 hr after 3-AP treatment show axon degeneration. Scale bars, 20 µm. FIG. 1C shows WT and Sarm1 KO embryonic DRGs were treated with 3-AP for 12 hr and MTT assays were performed to quantify cell viability at DIV7. Boxes represent the interquartile range with horizontal lines indicating the median and whisker lines extending to the maximum and minimum values. Statistical significance was determined by one-way ANOVA test, comparing to cell viability of each genotype treated with 0 µM 3-AP. **$p<0.0001$. FIG. 1D shows WT (top) and Sarm1 KO (bottom) DRGs were treated with 3-AP (300 µM) at DIV7. Axon degeneration index was measured at indicated times after 3-AP treatment. Data with error bars correspond to Mean±SD. Statistical significance was determined by one-way ANOVA tests, comparing to control degeneration index at time 0 hr. $p<0.0001$. FIG. 1E shows WT or Sarm1 KO DRG neurons were treated with 3-AP at DIV7. Metabolites were quantified by LC-MS/MS at indicated times after treatment. Data with error bars correspond to Mean±SD. Statistical significance was determined by one-way ANOVA tests, comparing to metabolite of each genotype at time 0 hr. $p<0.01$; *$p<0.001$; **$p<0.0001$.

FIG. 2A shows Nam inhibits 3-AP-induced axon degeneration. WT DRG neurons were pretreated overnight with Nam at 0, 50, 100 or 200 µM on DIV7, then treated with 3-AP (500 µM). Axon degeneration was quantified at indicated times following treatment. Data with error bars correspond to Mean±SD. Statistical significance was determined by one-way ANOVA tests (compared to 0 hr). *$p<0.001$; $p<0.0001$. FIG. 2B shows NAMPT inhibitor FK866 protects neurons against 3-AP toxicity. WT DRG neurons were pretreated overnight with FK866 at 0, 25, 50 or 100 nM, then treated with 3-AP (300 µM). Axon degeneration was quantified after 3-AP addition. Data with error bars correspond to Mean±SD. Statistical significance was determined by one-way ANOVA test (compared to 0 hr). *$p<0.001$; **$p<0.0001$. FIG. 2C, FIG. 2D, and FIG. 2E show metabolites in WT neurons treated as indicated were measured using LC-MS/MS. Data with error bars correspond to Mean±SD. FIG. 2F shows NMNAT1 prevents 3-AP-induced axon degeneration. WT DRG neurons were infected with NMNAT1 lentivirus at DIV3 and treated with 3-AP (300 µM) at DIV7. Data with error bars correspond to Mean±SD. Statistical significance was determined by one-way ANOVA test (compared to 0 hr). *$p<0.001$; **$p<0.0001$. FIG. 2G shows NMN deamidase fails to prevent 3-AP-induced axon degeneration. WT DRG neurons were infected with NMN deamidase (NMN DD) lentivirus at DIV3 and treated with 3-AP (300 µM) at DIV7. Data with error bars correspond to Mean±SD. Statistical significance was determined by one-way ANOVA test (compared to 0 hr). $p<0.01$; *$p<0.001$; **$p<0.0001$.

FIG. 3A shows 3-APAD is synthesized in 3-AP dose-dependent manner using in vitro reactions containing purified NAMPT and NMNAT1. Boxes represent the interquartile range with horizontal lines indicating the median and whisker lines extending to the maximum and minimum values. FIG. 3B show representative HPLC trace demonstrating the 3-AP dose-dependent production of 3-APAD in vitro via SARM1-mediated base exchange reaction.

FIG. 3C show in vitro 3-APAD production by SARM1 is dependent on $NAD^+$ concentration at a fixed 3-AP concentration (40 µM). Boxes represent the interquartile range with horizontal lines indicating the median and whisker lines extending to the maximum and minimum values. FIG. 3D shows in vitro 3-APAD production by SARM1 is dependent on 3-AP concentration at fixed $NAD^+$ concentration (50 µM). Boxes represent the interquartile range with horizontal lines indicating the median and whisker lines extending to the maximum and minimum values. FIG. 3E shows 3-APAD in neurons is produced by both SARM1 and the NAMPT/NMNAT pathway. WT, Sarm1 KO (SKO) and Nmnat2/Sarm1 double knockout (dKO) neurons were treated with 3-AP (300 µM) and metabolites were analyzed after 4 hr of treatment. Infection of dKO or SKO neurons with a SARM1 lentivirus increases the amount of 3-APAD detected. Boxes represent the interquartile range with horizontal lines indicating the median and whisker lines extending to the maximum and minimum values.

FIG. 4A shows fold-increase in rate of SARM1 hydrolase activity with increasing concentrations of 3-APMN (Mean±SD, n=3), as measured by PC6 fluorescence. FIG. 4B shows 3-APMN activates SARM1 via its $NMN/NAD^+$-binding pocket in the N-terminal domain. Sarm1 KO DRG neurons were infected with lentivirus expressing W103A, R157A or K193R SARM1 mutants or controls (GFP and wildtype SARM1) at DIV3. Axon degeneration indexes were determined at indicated times after 3-AP (300 µM) administration. Boxes represent the interquartile range with horizontal lines indicating the median and whisker lines extending to the maximum and minimum values. Statistical significance was determined by one-way ANOVA tests, comparing to degeneration index of 3-AP+GFP at each time point. ****$p<0.0001$.

FIG. 5A-FIG. 5F show 3-AP neurotoxicity in mice is mediated by SARM1. FIG. 5A shows the survival curve of WT and Sarm1 KO (SKO) mice injected IP with indicated doses of 3-AP (n=5). Mice injected with PBS (control) showed no lethality (n=3), and SKO mice injected with 275 mg/kg 3-AP showed no lethality (n=5). FIG. 5B shows cADPR levels in sciatic nerve of WT and SKO mice at 3 days post IP injection with PBS or 3-AP (275 mg/kg). Statistical significance was determined by one-way ANOVA tests, comparing to cADPR of WT PBS condition. Boxes represent the interquartile range with horizontal lines indicating the median and whisker lines extending to the maximum and minimum values. **p<0.0001. FIG. 5C shows immunofluorescent staining with antibodies against neurofilament (NF-200) or myelin basic protein (MBP) of tibial nerve cross sections from WT and Sarm1 KO animals in which the sciatic nerve was wrapped with Surgifoam soaked in 3-AP (500 mM) and corresponding contralateral untreated nerve. Scale bars, 25 μm. FIG. 5D shows images of toluidine blue-stained sections of tibial nerve treated with Surgifoam soaked in saline or 3-AP (500 mM) and corresponding contralateral untreated nerves. Scale bars, 10 μm. FIG. 5E shows quantification of axon counts relative to counts of saline treated nerve from toluidine blue-stained images. Boxes represent the interquartile range with horizontal lines indicating the median and whisker lines extending to the maximum and minimum values. NS, no significance; p<0.01. FIG. 5F show images of toluidine blue-stained sections of distal and proximal sciatic nerves from WT mice treated with Surgifoam soaked in 3-AP (500 mM). Similar findings were observed in 5/5 mice. Scale bars, 10 μm.

DETAILED DESCRIPTION

Figure 1A:
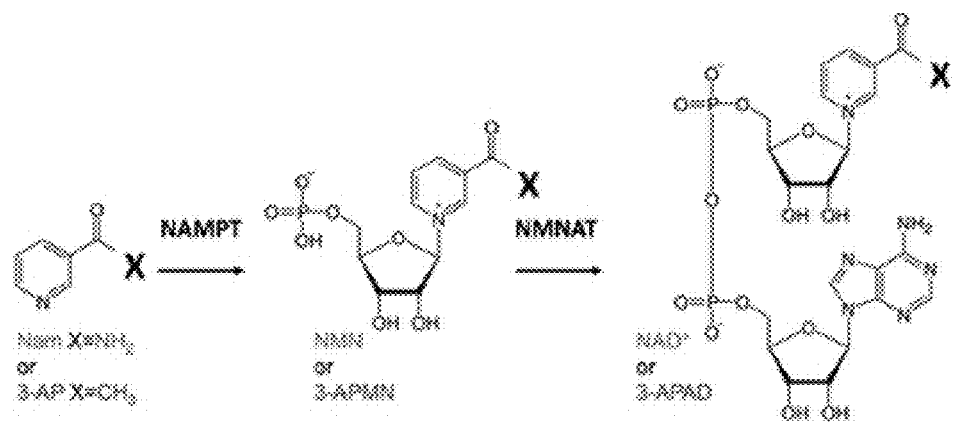
FIG. 1A-FIG. 1E show 3-AP causes SARM1-dependent neurotoxicity.

The present disclosure is based, at least in part, on the discovery of neuro-specific agents for therapeutic chemical neurolysis. As shown herein, therapeutic chemical agents and methods of detecting potentially therapeutic neuro-specific chemical agents have been identified. Current agents used for therapeutic chemical neurolysis can damage local tissues and cause systemic side effects which may limit their use.

Furthermore, the present disclosure provides compositions and methods to address a variety of muscle contraction diseases in addition to the cosmetic benefits. The neurolytic agents can be used to treat neuroma as a pain target or any disease where inhibition of sensory neurons is therapeutic (including topical application to the skin like a super capsacin). The presently described neurolytic agents include the three newly discovered SARM activators. Structural characteristics that have been discovered for an effective neurolytic agent can include containing a pyridine ring and being substrates for the nicotinamide phosphoribosyl transferase (NAMPT) enzyme to generate the mononucleotide version of the pyridine. The mononucleotide version of the pyridine is this version that binds to and activates SARM1.

Thus, the present disclosure is based, in part, on the discovery of a class of pyridine-derivatives which directly activate SARM1, the primary initiator of the programmed axon degeneration pathway, and that when applied locally to nerves, parent compounds of such derivatives provoke Wallerian degeneration of axons in the targeted nerves without causing systemic effects. SARM1 is activated by an endogenous agonist, nicotinamide mononucleotide (NMN). The present disclosure has discovered that certain pyridine-derivatives closely related to NMN, including 3-acetylpyridine mononucleotide (3-APMN), will also bind to and activate SARM1, initiating axon degeneration. Moreover, the present disclosure provides that cell-permeable parent compounds of these SARM1 activators, including 3-acetylpyridine (3-AP), the parent of 3-APMN, are metabolized intracellularly to generate their active metabolites. Another example of a pyridine-derivative SARM1 activator is 2-aminopyridine mononucleotide (2-APMN), which is generated from its cell permeable parent compound 2-aminopyridine (2-AP). In addition, vacor, can also be converted to its mononucleotide, VMN, and this compound also activates SARM1.

Therefore, these pyridine compounds are identified as useful to perform therapeutic neurolysis, a common treatment for neuropathic pain or headache, currently achieved using non-specific noxious agents. In addition, the present disclosure provides uses for the neurolytic agents beyond pain management, including, for example in facial paralysis. Patients who have had facial palsy, like Bells, that spontaneously improves often develop unwanted movements such as synkinesis. Thus, the compositions and methods of the disclosure can be used to weaken those unwanted movements and co-contractions that sometimes mask desired movements or cause functional problems. Patients can also have discomfort from hypertonicity of the buccinator muscle and can benefit from the neurolytic agents described herein. As another example, hemifacial spasm is another condition that can be treated by the neurolytic agent.

Because SARM1-activation specifically promotes axon degeneration, application of SARM1 activators are currently believed to not be harmful to non-neural tissues adjacent to a targeted nerve, such as muscle. The present disclosure shows that local administration of 3-AP does not affect other nerves outside the site of 3-AP application or cause systemic effects. Currently, the chemical agents used to produce therapeutic neurolysis, phenol and ethanol, are not neuro-specific, damage adjacent tissues, and can cause systemic side effects.

Described herein are methods to apply the SARM1 activators locally to the skin, in order to confirm that very narrowly-targeted local degeneration is possible. This would be akin to capsaicin treatment, but likely more potent and longer-lasting. Another interesting use case is painful neuroma, which includes inappropriate growths of sensory axons after injury or surgery. SARM1 activators applied to neuromas would selectively trigger their degeneration and may be more effective than current surgical approaches.

SARM1 activators according useful according to the disclosure include pyridines that are substrates for the nicotinamide phosphoribosyl transferase (NAMPT) enzyme. This would generate compound-MN. A mononucleotide (MN) is a single nucleotide. Therefore, it is a single unit comprised of one nucleobase, one pentose moiety, and phosphoric acid. This compound-MN should bind the allosteric pocket of SARM1 and activate the SARM1 NADase. In some aspects, the compound-MN is not a substrate for the next enzyme in the pathway, the enzyme nicotinamide mononucleotide adenyltransferase (NMNAT) so that no variants of $NAD^+$ are formed.

Also disclosed herein are methods for delivery of the compound in order to ensure local activation of SARM1. For example, skin ointment formulations can be appropriate, or nanoparticle encapsulation to reduce spread if injected locally (e.g., for neuroma treatment).

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules of the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Additional aspects of the disclosure are described below.

I. Compositions

One aspect of the present disclosure encompasses SARM1 activating neurolytic agents. As described herein, SARM1 is an inducible TIR-domain NAD$^+$ hydrolase that mediates pathological axon degeneration. SARM1 is activated by an increased ratio of NMN to NAD$^+$, which competes for binding to an allosteric activating site. When NMN binds, the TIR domain is released from autoinhibition, activating its NAD$^+$ hydrolase activity. As described herein, the SARM1 activating neurolytic agent can be an NAMPT substrate metabolized to form an NMN analog. As such, the SARM1 activating neurolytic agent can be a prodrug. For example, the SARM1 activating neurolytic agent can be a nicotinamide derivative.

In general, the compounds detailed herein include compounds comprising a substituted pyridine as SARM1 activating neurolytic agents, the general structure as diagrammed below. The pyridine chemical elements are expressed as $C_5H_{10}N$, and its synthesis is known. For example, pyridine and substituted derivates thereof can also be produced by a number of organic synthesis methods known in the art.

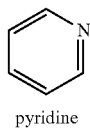

pyridine

Provided herein are substituted derivatives of pyridine. Pyridine substituted derivatives are modified versions of that are able to activate SARM1 mediated axon degeneration. In particular, the present disclosure provides pyridine compounds that are converted by NAMPT to a pyridine-mononucleotide that activates SARM1. In a non-limiting example, the substituted pyridine compound is nicotinamide (Nam) or an analog thereof.

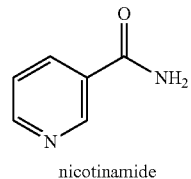

nicotinamide

In another non-limiting example, the substituted pyridine compound is 3-acetylpyridine (3-AP) or an analog thereof.

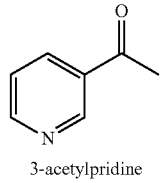

3-acetylpridine

In still another non-limiting example, the substituted pyridine compound is 2-aminopyridine or an analog thereof.

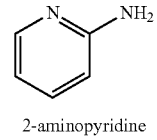

2-aminopyridine

In certain embodiments, the substituted pyridine is not 3-aminopyridine, 4-aminopyridine, 2-acetylpyridine, or 4-acetylpyridine.

The pyridine or analogs thereof can comprise or be substituted with R groups at one or more of the carbon atoms within the pyridine ring. R groups can be or can be optionally substituted with one or more groups independently selected from the group consisting of hydroxyl; $C_{1-10}$alkyl hydroxyl; amine; $C_{1-10}$carboxylic acid; $C_{1-10}$carboxyl; straight chain or branched $C_{1-10}$alkyl, optionally containing unsaturation; a $C_{2-10}$ cycloalkyl optionally containing unsaturation or one oxygen or nitrogen atom; straight chain or branched $C_{1-10}$alkyl amine; heterocyclyl; heterocyclic amine; and aryl comprising a phenyl; heteroaryl containing from 1 to 4 N, O, or S atoms; unsubstituted phenyl ring; substituted phenyl ring; unsubstituted heterocyclyl; and substituted heterocyclyl, wherein the unsubstituted phenyl ring or substituted phenyl ring can be optionally substituted with one or more groups independently selected from the group consisting of hydroxyl; $C_{1-10}$alkyl hydroxyl; amine; $C_{1-10}$carboxyl; $C_{1-10}$carboxylic acid; $C_{1-10}$carboxyl; straight chain or branched $C_{1-10}$alkyl, optionally containing unsaturation; straight chain or branched $C_{1-10}$alkyl amine, optionally containing unsaturation; a $C_{2-10}$cycloalkyl optionally containing unsaturation or one oxygen or nitrogen atom; straight chain or branched $C_{1-10}$alkyl amine; heterocyclyl; heterocyclic amine; aryl comprising a phenyl; and heteroaryl containing from 1 to 4 N, O, or S atoms; and the unsubstituted heterocyclyl or substituted heterocyclyl can be optionally substituted with one or more groups independently selected from the group consisting of hydroxyl; $C_{1-10}$alkyl hydroxyl; amine; $C_{1-10}$carboxylic acid; $C_{1-10}$carboxyl; straight chain or branched $C_{1-10}$alkyl, optionally containing unsaturation; straight chain or branched $C_{1-10}$alkyl amine, optionally containing unsaturation; a $C_{2-10}$ cycloalkyl optionally containing unsaturation or one oxygen or nitrogen atom; heterocyclyl; straight chain or branched $C_{1-10}$alkyl amine; heterocyclic amine; and aryl comprising a phenyl; and heteroaryl containing from 1 to 4 N, O, or S atoms. Any of the above can be further optionally substituted.

The term "imine" or "imino", as used herein, unless otherwise indicated, can include a functional group or chemical compound containing a carbon-nitrogen double bond. The expression "imino compound", as used herein, unless otherwise indicated, refers to a compound that includes an "imine" or an "imino" group as defined herein. The "imine" or "imino" group can be optionally substituted.

The term "hydroxyl", as used herein, unless otherwise indicated, can include —OH. The "hydroxyl" can be optionally substituted.

The terms "halogen" and "halo", as used herein, unless otherwise indicated, include a chlorine, chloro, $C_1$; fluorine, fluoro, F; bromine, bromo, Br; or iodine, iodo, or I.

The term "acetamide", as used herein, is an organic compound with the formula $CH_3CONH_2$. The "acetamide" can be optionally substituted.

The term "aryl", as used herein, unless otherwise indicated, include a carbocyclic aromatic group. Examples of aryl groups include, but are not limited to, phenyl, benzyl, naphthyl, or anthracenyl. The "aryl" can be optionally substituted.

The terms "amine" and "amino", as used herein, unless otherwise indicated, include a functional group that contains a nitrogen atom with a lone pair of electrons and wherein one or more hydrogen atoms have been replaced by a substituent such as, but not limited to, an alkyl group or an aryl group. The "amine" or "amino" group can be optionally substituted.

The term "alkyl", as used herein, unless otherwise indicated, can include saturated monovalent hydrocarbon radicals having straight or branched moieties, such as but not limited to, methyl, ethyl, propyl, butyl, pentyl, hexyl, octyl groups, etc. Representative straight-chain lower alkyl groups include, but are not limited to, -methyl, -ethyl, -n-propyl, -n-butyl, -n-pentyl, -n-hexyl, -n-heptyl and -n-octyl; while branched lower alkyl groups include, but are not limited to, -isopropyl, -sec-butyl, -isobutyl, -tert-butyl, -isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, unsaturated $C_1$-10 alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl,-1-butynyl, -2-butynyl, -1-pentynyl, -2-pentynyl, or -3-methyl-1 butynyl. An alkyl can be saturated, partially saturated, or unsaturated. The "alkyl" can be optionally substituted.

The term "carboxyl", as used herein, unless otherwise indicated, can include a functional group consisting of a carbon atom double bonded to an oxygen atom and single bonded to a hydroxyl group (—COOH). The "carboxyl" can be optionally substituted.

The term "carbonyl", as used herein, unless otherwise indicated, can include a functional group consisting of a carbon atom double-bonded to an oxygen atom (C=O). The "carbonyl" can be optionally substituted.

The term "alkenyl", as used herein, unless otherwise indicated, can include alkyl moieties having at least one carbon-carbon double bond wherein alkyl is as defined above and including E and Z isomers of said alkenyl moiety. An alkenyl can be partially saturated or unsaturated. The "alkenyl" can be optionally substituted.

The term "alkynyl", as used herein, unless otherwise indicated, can include alkyl moieties having at least one carbon-carbon triple bond wherein alkyl is as defined above. An alkynyl can be partially saturated or unsaturated. The "alkynyl" can be optionally substituted.

The term "acyl", as used herein, unless otherwise indicated, can include a functional group derived from an aliphatic carboxylic acid, by removal of the hydroxyl (—OH) group. The "acyl" can be optionally substituted.

The term "alkoxyl", as used herein, unless otherwise indicated, can include O-alkyl groups wherein alkyl is as defined above and O represents oxygen. Representative alkoxyl groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-methylbutyl, —O-2-methylpentyl, —O-3-methylpentyl, —O-2,2-dimethylbutyl, —O-2,3-dimethylbutyl, —O-2,2-dimethylpentyl, —O-2,3-dimethylpentyl, —O-3,3-dimethylpentyl, —O-2,3,4-trimethylpentyl, —O-3-methylhexyl, —O-2,2-dimethylhexyl, —O-2,4-dimethylhexyl, —O-2,5-dimethylhexyl, —O-3,5-dimethylhexyl, -0-2,4dimethylpentyl, —O-2-methylheptyl, —O-3-methylheptyl, —O-vinyl, —O-allyl, —O-1-butenyl, —O-2-butenyl, —O-isobutylenyl, —O-1-pentenyl, —O-2-pentenyl, —O-3-methyl-1-butenyl, —O-2-methyl-2-butenyl, —O-2,3-dimethyl-2-butenyl, —O-1-hexyl, —O-2-hexyl, —O-3-hexyl, —O-acetylenyl, —O-propynyl, —O-1-butynyl, —O-2-butynyl, —O-1-pentynyl, —O-2-pentynyl and —O-3-methyl-1-butynyl, —O-cyclopropyl, —O-cyclobutyl, —O-cyclopentyl, —O— cyclohexyl, —O-cycloheptyl, —O-cyclooctyl, —O-cyclononyl and —O-cyclodecyl, —O—$CH_2$-cyclopropyl, —O—$CH_2$-cyclobutyl, —O—$CH_2$-cyclopentyl, —O—$CH_2$-cyclohexyl, —O—$CH_2$-cycloheptyl, —O—$CH_2$-cyclooctyl, —O—$CH_2$-cyclononyl, —O—$CH_2$-cyclodecyl, —O—$(CH_2)_2$-cyclopropyl, —O—$(CH_2)_2$-cyclobutyl, —O—$(CH_2)_2$-cyclopentyl, —O—$(CH_2)_2$-cyclohexyl, —O—$(CH_2)_2$-cycloheptyl, —O—$(CH_2)_2$-cyclooctyl, —O—$(CH_2)_2$-cyclononyl, or —O—$(CH_2)_2$-cyclodecyl. An alkoxyl can be saturated, partially saturated, or unsaturated. The "alkoxyl" can be optionally substituted.

The term "cycloalkyl", as used herein, unless otherwise indicated, can include an aromatic, a non-aromatic, saturated, partially saturated, or unsaturated, monocyclic or fused, spiro or unfused bicyclic or tricyclic hydrocarbon referred to herein containing a total of from 1 to 10 carbon atoms (e.g., 1 or 2 carbon atoms if there are other heteroatoms in the ring), preferably 3 to 8 ring carbon atoms. Examples of cycloalkyls include, but are not limited to, $C_3$-10 cycloalkyl groups include, but are not limited to, -cyclopropyl, -cyclobutyl, -cyclopentyl, -cyclopentadienyl, -cyclohexyl, -cyclohexenyl,-1,3-cyclohexadienyl, -1,4-cyclohexadienyl, -cycloheptyl, -1,3-cycloheptadienyl, -1,3,5- cycloheptatrienyl, -cyclooctyl, and -cyclooctadienyl. The term "cycloalkyl" also can include -lower alkyl-cycloalkyl, wherein lower alkyl and cycloalkyl are as defined herein. Examples of -lower alkyl-cycloalkyl groups include, but are not limited to, —CH₂-cyclopropyl, —CH₂-cyclobutyl, —CH₂-cyclopentyl, —CH₂-cyclopentadienyl, —CH₂-cyclohexyl, —CH₂-cycloheptyl, or —CH₂-cyclooctyl. The "cycloalkyl" can be optionally substituted. A "cycloheteroalkyl", as used herein, unless otherwise indicated, can include any of the above with a carbon substituted with a heteroatom (e.g., O, S, N).

The term "heterocyclic" or "heteroaryl", as used herein, unless otherwise indicated, can include an aromatic or non-aromatic cycloalkyl in which one to four of the ring carbon atoms are independently replaced with a heteroatom from the group consisting of O, S, and N. Representative examples of a heterocycle include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl, or tetrazolyl. Heterocycles can be substituted or unsubstituted. Heterocycles can also be bonded at any ring atom (i.e., at any carbon atom or heteroatom of the heterocyclic ring). A heterocyclic can be saturated, partially saturated, or unsaturated. The "heterocyclic" can be optionally substituted.

The term "indole", as used herein, is an aromatic heterocyclic organic compound with formula $C_8H_7N$. It has a bicyclic structure, consisting of a six-membered benzene ring fused to a five-membered nitrogen-containing pyrrole ring. The "indole" can be optionally substituted.

The term "cyano", as used herein, unless otherwise indicated, can include a —CN group. The "cyano" can be optionally substituted.

The term "alcohol", as used herein, unless otherwise indicated, can include a compound in which the hydroxyl functional group (—OH) is bound to a carbon atom. In particular, this carbon center should be saturated, having single bonds to three other atoms. The "alcohol" can be optionally substituted.

As disclosed herein, a substituted pyridine compound useful according to the disclosure, i.e. as a SARM1 activating neurolytic agent, are those which are substrates of nicotinamide phosphoribosyl transferase, thereby catalyzing the mononucleotide addition to the substituted pyridine compounds. Thus, a substituted pyridine compound useful according to the disclosure comprise those which have been mononucleotide modified. In a non-limiting example, the SARM1 activating neurolytic agent is nicotinamide mononucleotide (NMN) or an analog thereof.

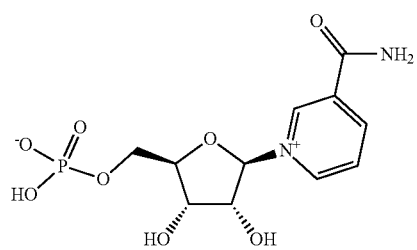

In another non-limiting example, the SARM1 activating neurolytic agent is 3-acetylpyridine mononucleotide or an analog thereof.

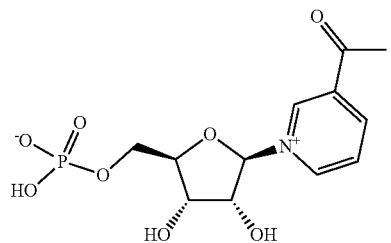

In still another non-limiting example, the SARM1 activating neurolytic agent is 2-aminopyridine mononucleotide or an analog thereof.

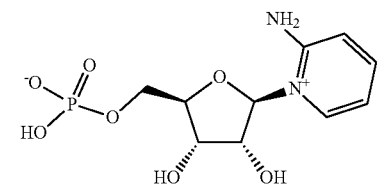

In another aspect, SARM1 activating neurolytic agent or prodrug thereof can be vacor,

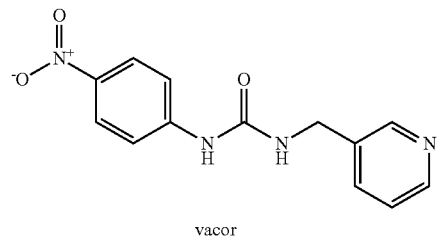

vacor

In still another aspect, SARM1 activating neurolytic agent or prodrug thereof can be vacor mononucleotide (VMN).

The discovery of this allosteric activating site led to the testing of other NAD⁺-related metabolites that can activate SARM1. The present disclosure shows that the nicotinamide analog 3-acetylpyridine (3-AP), is converted to 3-APMN, which activates SARM1 and induces SARM1-dependent NAD⁺ depletion, axon degeneration, and neuronal death of cultured neurons. Systemic treatment with 3-AP causes rapid SARM1-dependent death, while local application to peripheral nerve induces SARM1-dependent local axon degeneration. A related pyridine derivative, 2-aminopyridine is also identified as another SARM1-dependent neurotoxin. It was also discovered that Pyrinuron (N-(4-Nitrophenyl)-N'-[(pyridin-3-yl)methyl]urea) a.k.a. Vacor, is an NAMPT substrate metabolized to form an NMN analog which triggers SARM1-dependent axon degeneration. These findings identify SARM1 as a candidate mediator of environmental neurotoxicity, and furthermore, suggest that SARM1 agonists can be developed into selective agents for neurolytic therapy.

Other compounds that were tested, but did not work include 3-aminopyridine, 4-aminopyridine, 2-acetylpyridine, and 4-acetylpyridine. As such, these methods for finding activators are good because they are specific and can distinguish among similar compounds.

A pyridine derivative, as discussed above, may be modified further modified to improve potency, bioavailability, solubility, stability, handling properties, or a combination thereof, as compared to an unmodified version. Thus, in another aspect, a composition of the invention comprises modified pyridine derivative. In still another aspect, a composition of the invention comprises a prodrug of a pyridine derivative.

A composition of the invention may optionally comprise one or more additional drug or therapeutically active agent in addition to the SARM1 activating neurolytic agent. A composition of the invention may further comprise a pharmaceutically acceptable excipient, carrier, or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents, or antioxidants.

Dosages of a SARM1 activating neurolytic agent can vary between wide limits, depending upon the disease or disorder to be treated, the age and condition of the subject to be treated. In an embodiment where a composition comprising a compound of SARM1 activating neurolytic agent is contacted with a sample, the concentration of a SARM1 activating neurolytic agent may be from about 0.1 µM to about 40 µM. Alternatively, the concentration of a SARM1 activating neurolytic agent may be from about 5 µM to about 25 µM. For example, the concentration of a SARM1 activating neurolytic agent may be about 0.1, about 0.25, about 0.5, about 0.6, about 0.7, about 0.8, about 0.9, about 1, about 2.5, about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 35, or about 40 µM. Additionally, the concentration of a SARM1 activating neurolytic agent may be greater than 40 µM. For example, the concentration of a SARM1 activating neurolytic agent may be about 40, about 45, about 50, about 55, about 60, about 65, about 70, about 75, about 80, about 85, about 90, about 95, or about 100 µM.

In an embodiment where the composition comprising a compound of Formula (I) is administered to a subject, the dose of a SARM1 activating neurolytic agent may be from about 0.1 mg/kg to about 500 mg/kg. For example, the dose of a SARM1 activating neurolytic agent may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of a SARM1 activating neurolytic agent may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of a SARM1 activating neurolytic agent may be about 300 mg/kg, about 325 mg/kg, about 350 mg/kg, about 375 mg/kg, about 400 mg/kg, about 425 mg/kg, about 450 mg/kg, about 475 mg/kg or about 500 mg/kg.

(a) Components of the Composition

The present disclosure also provides pharmaceutical compositions. The pharmaceutical composition comprises a SARM1 activating neurolytic agent, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In each of the embodiments described herein, a composition of the invention may optionally comprise one or more additional drug or therapeutically active agent in addition to the SARM1 activating neurolytic agent. In some embodiments, the additional drug or therapeutically active agent induces anti-inflammatory effects or is capable of protecting surround tissues. In some embodiments, the secondary agent is an antibody. In some embodiments, the secondary agent is selected from a corticosteroid, a non-steroidal anti-inflammatory drug (NSAID), an intravenous immunoglobulin, a tyrosine kinase inhibitor, a fusion protein, a monoclonal antibody directed against one or more pro-inflammatory cytokines, a chemotherapeutic agent and a combination thereof.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(b) Administration (i) Dosage Forms

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a SARM1 activating neurolytic agent, is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a SARM1 activating neurolytic agent, in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the SARM1 activating neurolytic agent may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying PFD, PFD derivative, a SARM1 activating neurolytic agent, may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of SARM1 activating neurolytic agent, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The SARM1 activating neurolytic agent may be encapsulated in a microemulsion by any method generally known in the art.

In yet another embodiment, a SARM1 activating neurolytic agent, may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Methods

The present disclosure encompasses a method of activating SARM1 mediated axon degeneration, the method comprising providing a SARM1 activating agent, for instance those described in Section I and incorporated into this section by reference. In another aspect, the present disclosure encompasses a method of therapeutic neurolysis in a subject in need thereof, the method comprising administering to the subject a composition comprising a therapeutically effective amount of a SARM1 activating agent. In yet another aspect, the present disclosure provides a composition comprising a SARM1 activating agent, for use in vitro, in vivo, or ex vivo. Suitable compositions comprising a SARM1 activating agent disclosed herein.

As described herein, the SARM1 activating agents can target nerve fibers, such as sensory fibers, but can also target motor fibers (e.g., to treat spasms). Thus, the presently disclosed SARM1 activators can act on motor axons, like Botox, but can act as "Botox for sensory axons." The agents and methods described herein can be used in place of botox. Botox can be non-specific and have batch to batch variability. The effects of the neurolytic agents would also last longer than botox. These SARM1 activating neurolytic agents are more specific, have longer-lasting effects, and would not have the same batch variability as botox and other botox-related products. As such, these neurolytic agents can be used wherever botox is currently used. Advantages of the neurolytic agents described herein include longer-lasting effects than botox or other botox-related agents. As such, the SARM1 activators can be used for targeting motor fibers for motor or muscle contraction conditions, such as those treated by botox.

Botox injections are noted primarily for the ability to reduce the appearance of facial wrinkles. They're also used to treat conditions such as neck spasms (cervical dystonia), excessive sweating (hyperhidrosis), an overactive bladder, and lazy eye. Botox injections may also help prevent chronic migraines.

Thus, the method of the present disclosure include, administering a SARM1 activating agent of the disclosure to a subject for treating wrinkles, cervical dystonia, lazy eye, muscle contractures, hyperhidrosis, chronic migraine, bladder dysfunction, or chronic migraine.

Cervical dystonia. In this painful condition, your neck muscles contract involuntarily causing your head to twist or turn into an uncomfortable position.

Lazy eye. The most common cause of lazy eye is an imbalance in the muscles responsible for positioning the eye.

Muscle contractures. Some neurological conditions, such as cerebral palsy, can cause your limbs to pull in toward your center. In some cases, these contracted muscles can be relaxed with Botox injections.

Hyperhidrosis. In this condition, excessive sweating occurs even when the temperature isn't hot and you're not exerting yourself.

Chronic migraine. If you experience migraines more than 15 days a month, Botox injections may help reduce headache frequency.

Bladder dysfunction. Botox injections can also help reduce urinary incontinence caused by an overactive bladder.

Eye twitching. Botox injections may help relieve contracture or twitching of muscles around the eye.

Also provided is are methods of treating, preventing, or reversing any disease, disorder, or condition where inhibition of sensory neurons is therapeutic (e.g., pain conditions, neuropathic pain (e.g., with late-stage cancer), muscle contraction diseases, neuroma, pain, post-surgical pain, post-amputation pain, post-traumatic pain, cosmetic, facial paralysis, facial palsy (e.g., Bells), synkinesis, hypertonicity of the buccinator muscle, hemifacial spasm, reduce facial wrinkles, neck spasms (cervical dystonia), excessive sweating (hyperhidrosis), an overactive bladder, lazy eye, eye twitching, chronic migraines) in a subject in need of administration of a therapeutically effective amount of a SARM1 activating neurolytic agent, so as to initiate, trigger, or promote axon degeneration (or degeneration of sensory pain fibers, axons, neurolysis).

Methods described herein are generally performed on a subject in need thereof. A subject in need of the therapeutic methods described herein can be a subject having, diagnosed with, suspected of having, or at risk for developing any disease, disorder, or condition where inhibition of sensory neurons is therapeutic. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of a SARM1 activating neurolytic agent is, for example, an amount that would cause the desired therapeutic effect in a subject while minimizing undesired side effects. In various embodiments, an effective amount of a SARM1 activating neurolytic agent described herein can substantially initiate, trigger, or promote axon degeneration (or degeneration of sensory pain fibers).

According to the methods described herein, administration can be parenteral, pulmonary, oral, topical, intradermal, intramuscular, intraperitoneal, intravenous, intratumoral, intrathecal, intracranial, intracerebroventricular, subcutaneous, intranasal, epidural, ophthalmic, buccal, or rectal administration. Any of these agents, drug delivery systems, or methods can be used in or for a topical or transdermal formulation. Any method or system described in the Review Braz. J. Pharm. Sci. 52 (03) September 2016 can be used.

When used in the treatments described herein, a therapeutically effective amount of a SARM1 activating neurolytic agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to initiate, trigger, or promote axon degeneration (or degeneration of sensory pain fibers).

The amount of a composition described herein that can be combined with a pharmaceutically acceptable carrier to produce a single dosage form will vary depending upon the subject or host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the LD50 (the dose lethal to 50% of the population) and the ED50, (the dose therapeutically effective in 50% of the population). The dose ratio between toxic and therapeutic effects is the therapeutic index that can be expressed as the ratio LD50/ED50, where larger therapeutic indices are generally understood in the art to be optimal.

The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing, reversing, or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or a physician.

Administration of a SARM1 activating neurolytic agent can occur as a single event or over a time course of treatment. For example, a SARM1 activating neurolytic agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to or before, concurrent with, or after conventional treatment modalities for pain conditions, muscle contraction diseases, neuroma, pain, cosmetic, facial paralysis, facial palsy (e.g., Bells), synkinesis, hypertonicity of the buccinator muscle, hemifacial spasm, reduce facial wrinkles, neck spasms (cervical dystonia), excessive sweating (hyperhidrosis), an overactive bladder, lazy eye, eye twitching, or chronic migraines.

A SARM1 activating neurolytic agent can be administered simultaneously or sequentially with another agent, such as an antibiotic, an anti-inflammatory, or another agent. For example, a SARM1 activating neurolytic agent can be administered simultaneously with another agent, such as an antibiotic or an anti-inflammatory. Simultaneous administration can occur through administration of separate compositions, each containing one or more of a SARM1 activating neurolytic agent, an antibiotic, an anti-inflammatory, or another agent. Simultaneous administration can occur through administration of one composition containing two or more of a SARM1 activating neurolytic agent, an antibiotic, an anti-inflammatory, or another agent. A SARM1 activating neurolytic agent can be administered sequentially with an antibiotic, an anti-inflammatory, or another agent. For example, a SARM1 activating neurolytic agent can be administered before or after administration of an antibiotic, an anti-inflammatory, or another agent.

Also provided are screening methods to identify SARM1 activating agents or prodrugs thereof. In some embodiments, a SARM1 activating agent can be identified by screening for, or identifying and validating potential SARM1 activators (test compounds, for example from a library) useful for therapeutic neurolysis. For example, the screening can include measuring SARM1 activation directly in vitro using a fluorescent SARM1 activity probe; measuring cADPR, a specific biomarker of SARM1 activity; assaying axon degeneration in genetically modified mouse neurons that lack SARM1; and/or assaying the requirement of the SARM1 allosteric pocket for the efficacy of the potential SARM1 activators.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 MW, or less than about 1000 MW, or less than about 800 MW) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl, or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example, ChemBridge, Princeton BioMolecular, Ambinter SARL, Enamine, ASDI, Life Chemicals, etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical success if it is drug-like.

Several of these "drug-like" characteristics have been summarized into the four rules of Lipinski (generally known as the "rules of fives" because of the prevalence of the number 5 among them). While these rules generally relate to oral absorption and are used to predict the bioavailability of a compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

III. Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to SARM1 activating agents including prodrugs of the agents. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline each of which has been packaged under a neutral non-reacting gas, such as nitrogen. Ampules may consist of any suitable material, such as glass, organic polymers, such as polycarbonate, polystyrene, ceramic, metal, or any other material typically employed to hold reagents. Other examples of suitable containers include bottles that may be fabricated from similar substances as ampules and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or another substrate, and/or may be supplied as an electronic-readable medium or video. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported a precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook, et al., 1989) Cold Spring Harbor Press; Oligonucleotide Synthesis (M. J. Gait, ed. 1984); Methods in Molecular Biology, Humana Press; Cell Biology: A Laboratory Notebook (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); DNA Cloning: A practical Approach, Volumes I and II (D. N. Glover ed. 1985); Nucleic Acid Hybridization (B.

D. Hames & S. J. Higgins eds.(1985»; Transcription and Translation (B. D. Hames & S. J. Higgins, eds. (1984»; Animal Cell Culture (R. I. Freshney, ed. (1986»; Immobilized Cells and Enzymes (IRL Press, (1986»; and B. Perbal, A practical Guide To Molecular Cloning (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Neurotoxins Subvert the Allosteric Activation Mechanism of SARM1 to Induce Neuronal Loss SARM1 is an inducible TIR-domain $NAD^+$ hydrolase that mediates pathological axon degeneration. SARM1 is activated by an increased ratio of NMN to $NAD^+$, which competes for binding to an allosteric activating site. When NMN binds, the TIR domain is released from autoinhibition, activating its $NAD^+$ hydrolase activity. The discovery of this allosteric activating site led to the investigation of whether other $NAD^+$-related metabolites activate SARM1. The present example shows the nicotinamide analogue 3-acetylpyridine (3-AP), first identified as a neurotoxin in the 1940s, is converted to 3-APMN which activates SARM1 and induces SARM1-dependent $NAD^+$ depletion, axon degeneration and neuronal death. In mice, systemic treatment with 3-AP caused rapid SARM1-dependent death, while local application to peripheral nerve induces SARM1-dependent axon degeneration. The present example identifies 2-aminopyridine as another SARM1-dependent neurotoxin. These findings identify SARM1 as a candidate mediator of environmental neurotoxicity, and suggest that SARM1 agonists are useful for selective agents in neurolytic therapy.

Results

3-AP induces SARM1-dependent axon degeneration and neuron death: 3-acetyl-pyridine (3-AP) is an analog of nicotinamide (Nam) in which the amino group is replaced by a methyl group (FIG. 1A). 3-AP was previously studied as an anti-metabolite in $NAD^+$ biosynthesis, and assumed to produce its effects by disrupting the conversion of Nam to NMN and ultimately $NAD^+$. Early studies showed that administration of 3-AP to rabbits, dogs, mice and rats resulted in severe neurotoxicity and death that could be blocked by administration of Nam.

Figure 1B:
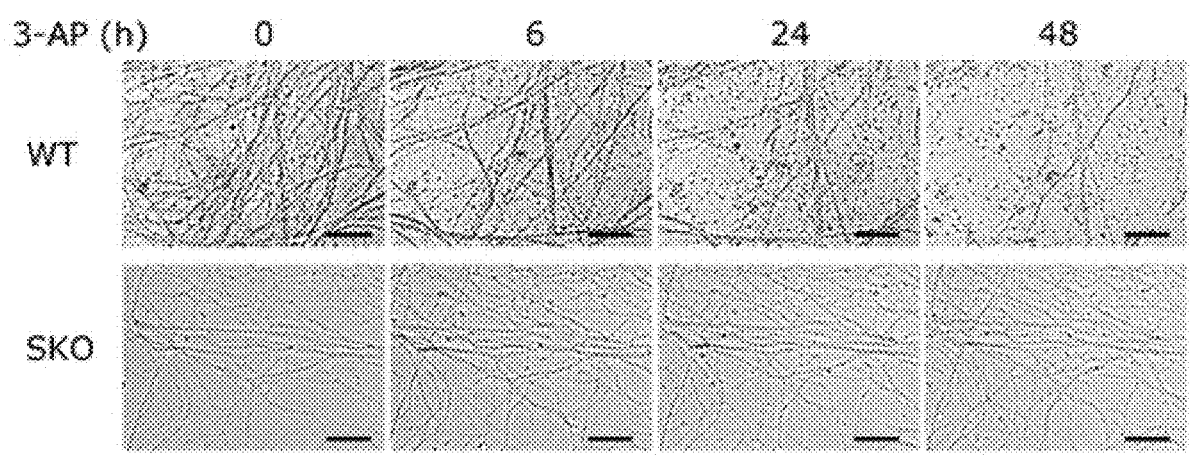
Figure 1C:
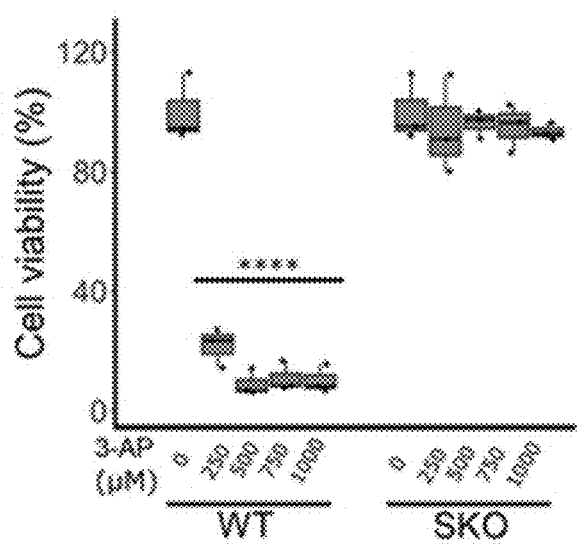
Figure 1D:
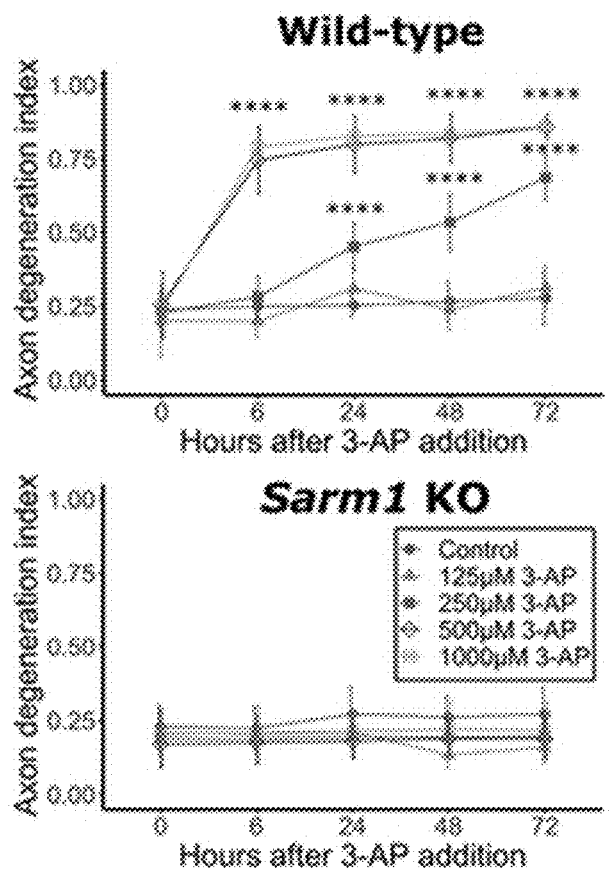

The recent demonstration that NMN binds to an allosteric site in SARM1 to activate its $NAD^+$ hydrolase activity and promote axon degeneration led to the examination of the role of SARM1 in 3-AP toxicity. WT mouse embryonic dorsal root ganglion (DRG) neurons were cultured and treated with varying doses of 3-AP. Axonal integrity was measured at multiple time points after 3-AP addition and it was found that axons remain intact at low doses, but begin to degenerate slowly when exposed to 250 µM 3-AP. At doses above 250 µM, axons rapidly degenerate at a rate similar to that observed after transection (FIG. 1B and FIG. 1D). Neuronal death was also measured using the MTT assay and it was found that 3-AP treatment causes neuronal death at similar doses (FIG. 1C).

SARM1 is required for pathological axon degeneration downstream of multiple insults and, when activated throughout the cell, also induces neuronal cell death. It was tested whether 3-AP-mediated axon degeneration and neuronal death also require SARM1 by treating Sarm1 KO DRG neurons with escalating doses of 3-AP. Surprisingly, it was found that 3-AP has no effect on neurons lacking SARM1 (FIG. 1C and FIG. 1D), even at extremely high doses (e.g., 1 mM). These experiments demonstrated that 3-AP mediated neurotoxicity requires SARM1.

Figure 1E:
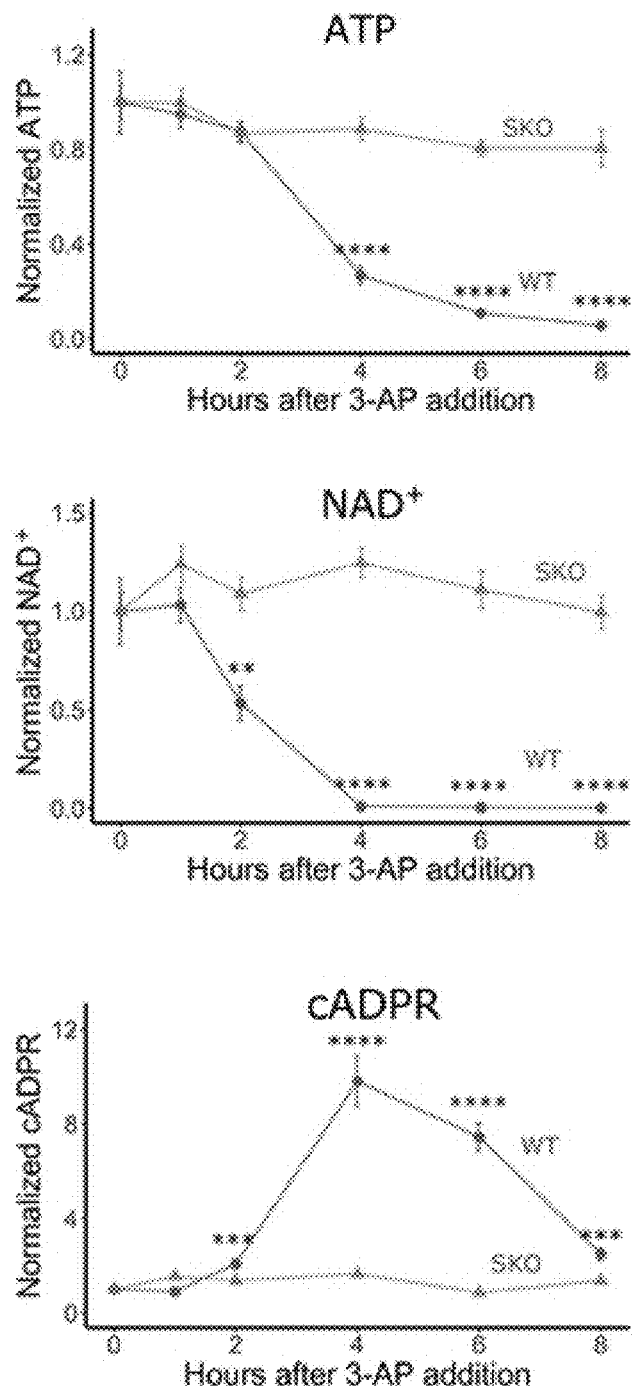

When SARM1 is activated by axonal injury, its potent $NAD^+$ hydrolase activity depletes the axon of $NAD^+$ and produces cADPR, a sensitive biomarker of SARM1 activity. These metabolic changes incite energetic catastrophe and subsequent axon fragmentation. To determine whether 3-AP activates SARM1 $NAD^+$ hydrolase activity, relevant metabolites were measured in neurons following addition of 3-AP (300 µM). Substantial $NAD^+$ and ATP depletion was found and a -10-fold increase in cADPR at 4 hr post 3-AP addition (FIG. 1E). These metabolite changes are similar to those observed after axotomy and indicate that SARM1 is activated by 3-AP. To confirm the SARM1-dependence of 3-AP neurotoxicity, similar metabolite measurements in 3-AP-treated Sarm1 KO neurons were performed and no significant changes in the levels of $NAD^+$, ATP, or cADPR were found (FIG. 1E). Taken together, these results demonstrate that 3-AP stimulates metabolite changes consistent with SARM1 activation, and that 3-AP neurotoxicity is dependent on SARM1.

Figure 2A:
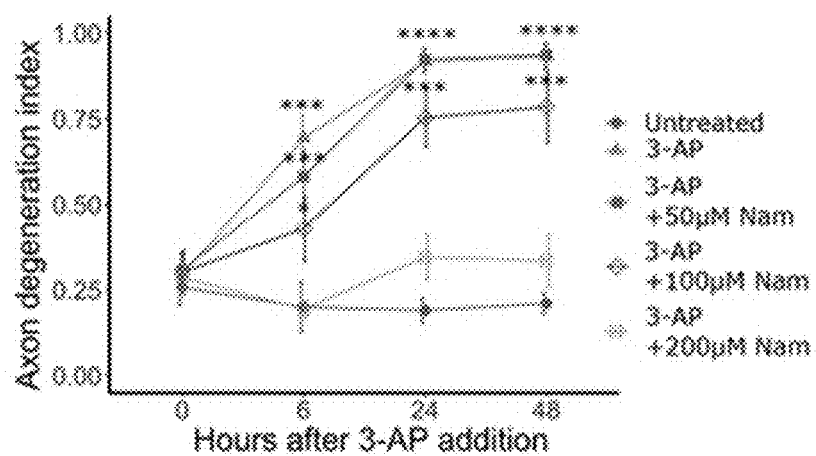
FIG. 2A-2G show the conversion of 3-AP to 3-APMN is required for neurotoxicity.
Figure 2B:
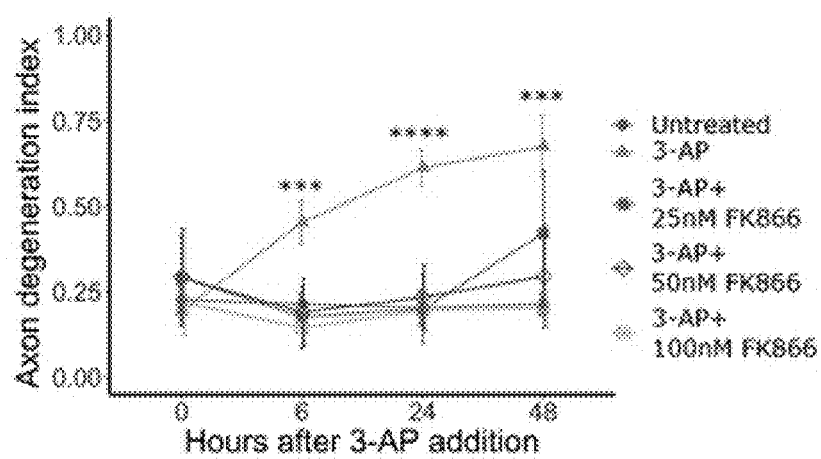

Neurotoxicity caused by 3-AP requires its conversion to 3-APMN: While the metabolic changes induced by 3-AP are almost identical to those caused by axotomy, there is one telling difference. Following axotomy, NMN levels rise because axonal NMNAT2 is lost. In contrast, 3-AP intoxication leads to a greater than 50% decline in NMN within four hours ($p<0.001$, n=3). As NMN is synthesized from Nam and PRPP by the enzyme NAMPT, this finding suggests that 3-AP competes with Nam for NAMPT, and thereby inhibits the production of NMN. Early studies of 3-AP neurotoxicity in mice and other species provide additional evidence for competition between 3-AP and Nam. These studies showed that co-administration of Nam prevented 3-AP-induced neurotoxicity and death. To assess whether Nam influences 3-AP-mediated axon degeneration, DRG neurons were pretreated with increasing amounts of Nam before addition of 3-AP. Nam pretreatment reduces 3-AP-induced axon degeneration in a dose-dependent manner (FIG. 2A), suggesting that Nam blocks the metabolism of 3-AP into a compound toxic to axons. A similar protective effect was observed for neuronal cell death (as quantified in FIG. 1C), confirming the concordance of soma and axonal demise in response to global SARM1 activation. As an independent test of this hypothesis, we treated neurons with 3-AP and FK866, an inhibitor of NAMPT. NAMPT inhibition blocks the neurotoxic actions of 3-AP (FIG. 2B), supporting the idea that 3-AP is metabolized to a toxic derivative via a pathway involving NAMPT.

Figure 2C:
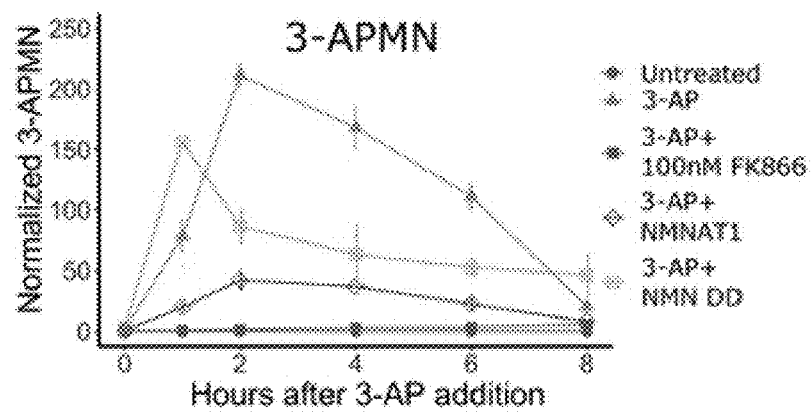
Figure 2D:
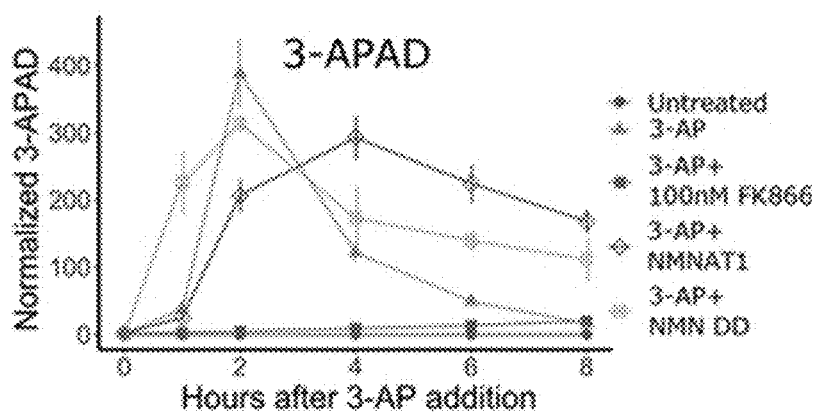
Figure 2E:
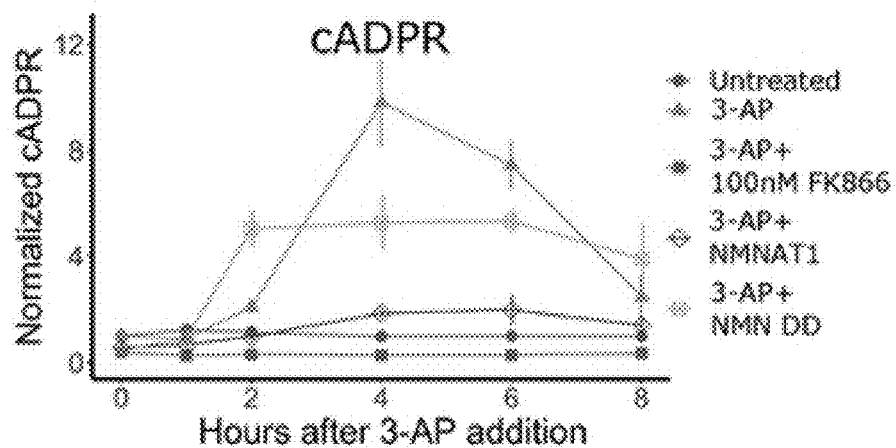

To identify the 3-AP derivative responsible for SARM1 activation and axon degeneration, mass spectrometry methods were first developed to detect 3-acetylpyridine mononucleotide (3-APMN) and 3-acetylpyridine adenine dinucleotide (3-APAD) in neurons. metabolites from DRG neurons were isolated at various timepoints following 3-AP treatment and analyzed them by LC-MS/MS. Both 3-APMN and 3-APAD levels peak within 2 hr of 3-AP addition, with 3-APMN detectable slightly earlier than 3-APAD consistent with a precursor-product relationship (FIG. 2C and FIG. 2D). Notably, they both appear several hours before the increase of the SARM1-derived product cADPR (FIG. 2E).

To demonstrate directly the involvement of NAMPT/NMNAT activity in the production of these metabolites, neurons were pre-treated with FK866 prior to 3-AP addition. In FK866-treated neurons, 3-APMN and 3-APAD remain at baseline, and cADPR levels do not increase (FIG. 2C, FIG. 2D and FIG. 2E). Together with results demonstrating FK866 blocks axon degeneration in 3-AP treated neurons, these data strongly support the hypothesis that 3-AP is metabolized by NAMPT alone or in combination with other $NAD^+$ biosynthetic enzymes (e.g., NMNAT) to produce a SARM1 agonist.

Figure 2F:
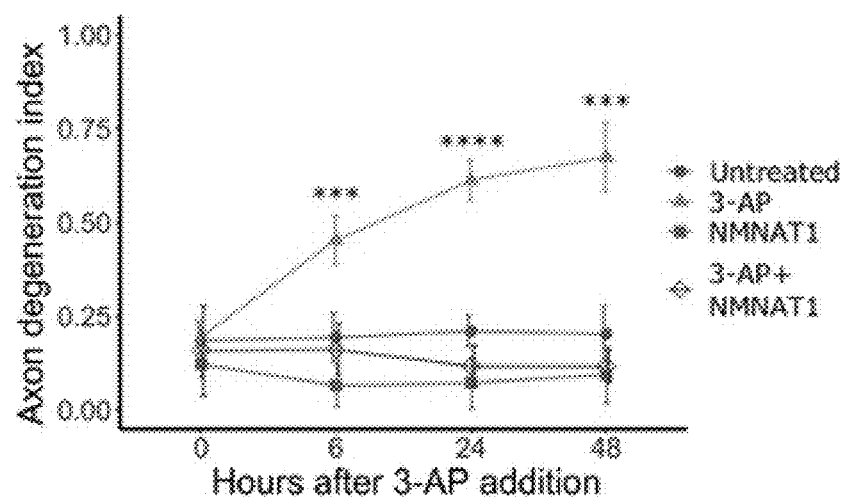
Figure 2G:
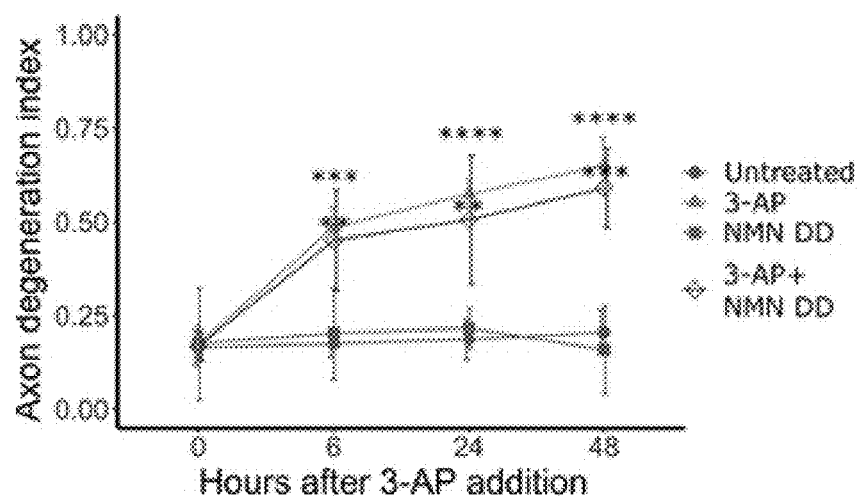

SARM1-mediated axon degeneration caused by mechanical or chemical insults can be blocked by overexpression of NMNAT1 or the bacterial enzyme NMN deamidase. The axon protection provided by these enzymes presumably reflects their ability to reduce axonal NMN levels via conversion of NMN to $NAD^+$ or NaMN, respectively. When NMN levels are low, it is less likely to bind the SARM1 allosteric site and induce the conformational change that activates SARM1 hydrolase activity and subsequent axon degeneration. To investigate which 3-AP-derived metabolite activates SARM1, NMN-consuming enzymes which could also ameliorate 3-AP neurotoxicity were tested. NMNAT1 prevents 3-AP-induced increases in cADPR and axon fragmentation (FIG. 2E and FIG. 2F). In contrast, axons of neurons expressing NMN deamidase remain susceptible to 3-AP and high levels of cADPR are produced (FIG. 2E and FIG. 2G). In each case, 3-AP stimulated neuron cell death was affected similarly as axon degeneration. Importantly, 3-APMN and 3-APAD are still generated in the presence of NMN deamidase (FIG. 2C and FIG. 2D). This is consistent with its deamidase activity, as 3-AP derivatives lack the amino group that is the target of this enzyme in Nam. In contrast, NMNAT1 overexpression strongly blunts the rise of both 3-APMN and cADPR while maintaining robust production of 3-APAD (FIG. 2C, FIG. 2D, and FIG. 2E), indicating that SARM1 is not activated when 3-APMN levels are low. These results support the hypothesis that 3-APMN is the 3-AP derivative that directly activates SARM1 to drive neuronal cell death and axon fragmentation.

Figure 3A:
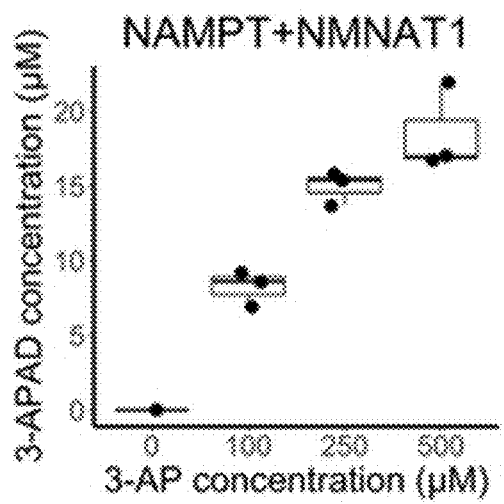
FIG. 3A-3E show 3-APAD can be generated by either NAMPT-NMNAT pathway or SARM1-mediated base exchange reaction.

3-AP can be converted to 3-APMN and 3-APAD by NAMPT and NMNAT: The inhibition of NAMPT and overexpression of NMNAT1 both prevent 3-AP mediated SARM1 activation and neuronal toxicity. These results along with the structural similarities between Nam and 3-AP and their respective metabolites, NMN and 3-APMN, led us to hypothesize that NAMPT converts 3-AP to 3-APMN, which then acts as an NMN mimetic to directly activate SARM1-mediated axon degeneration. It was first tested whether NAMPT can convert 3-AP to 3-APMN using an in vitro biochemical assay. NAMPT enzyme was produced in *E. coli* and the purified enzyme was incubated with 3-AP and its cofactors phosphoribosyl pyrophosphate (PRPP) and ATP. LC-MS/MS was used to detect the compound generated in this reaction, which was determined to be 3-APMN. Next, whether this 3-APMN could be converted to 3-APAD by NMNAT1 was examined. NMNAT1 was produced and purified and reactions in which NAMPT and NMNAT1 together were combined with 3-AP, PRPP and ATP were performed. A compound that was identified as 3-APAD was detected using a 3-APAD standard and LC-MS/MS (FIG. 3A). The production and identification of these two 3-AP derived products confirms that 3-AP can be metabolized by the NAMPT/NMNAT pathway in a parallel fashion to Nam.

Figure 3B:
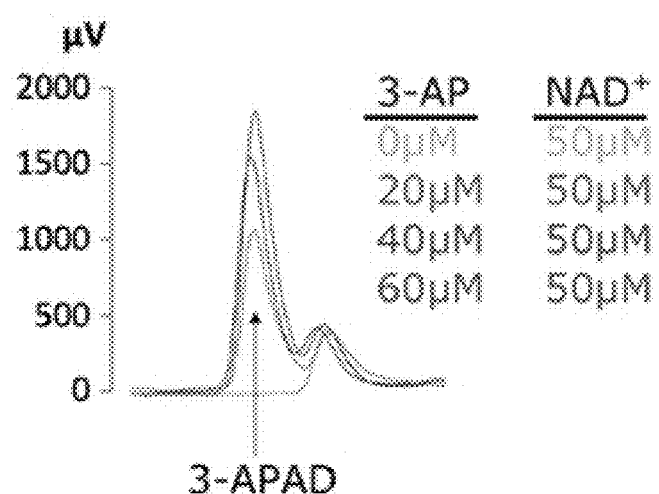
Figure 3C:
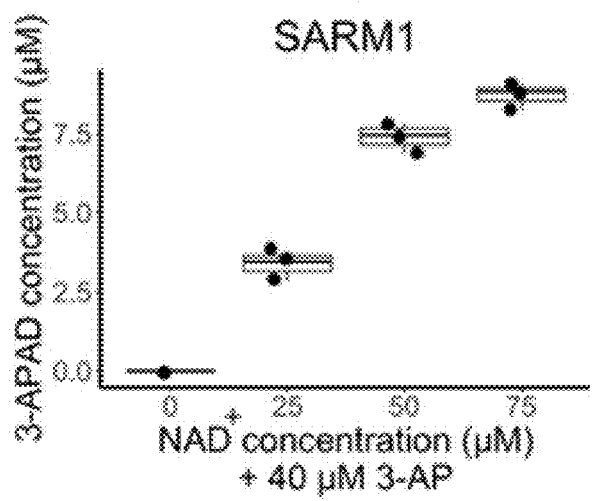
Figure 3D:
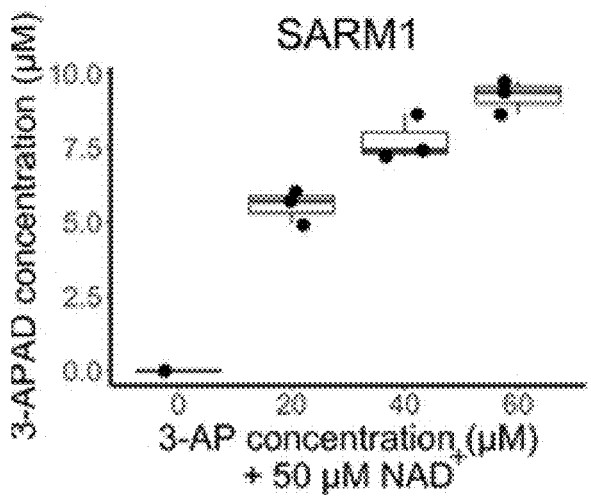

SARM1 also synthesizes 3-APAD from 3-AP and $NAD^+$ via base exchange: SARM1 possesses base exchange activity in addition to its hydrolase activity, in which the ADPR moiety of $NAD^+$ is condensed with an acceptor molecule. This reaction presents a pathway for the direct production of 3-APAD by SARM1 using 3-AP as the acceptor. To test this idea, biochemical assays were performed using SARM1 purified from HEK 293T cells. SARM1 was incubated with $NAD^+$ and 3-AP and the reaction products were analyzed using HPLC and LC-MS/MS. the formation of 3-APAD by SARM1 was detected (FIG. 3B) that required both $NAD^+$ and 3-AP with the amount of product dependent on the concentrations of both precursors. (FIG. 3C and FIG. 3D). The formation of 3-APAD from 3-AP is consistent with the SARM1 catalyzed transfer of the $NAD^+$ ADPR moiety to 3-AP via a base exchange reaction. This represents a second route for production of 3-APAD from 3-AP that is in addition to the NAMPT/NMNAT1 pathway (FIG. 3A).

Figure 3E:
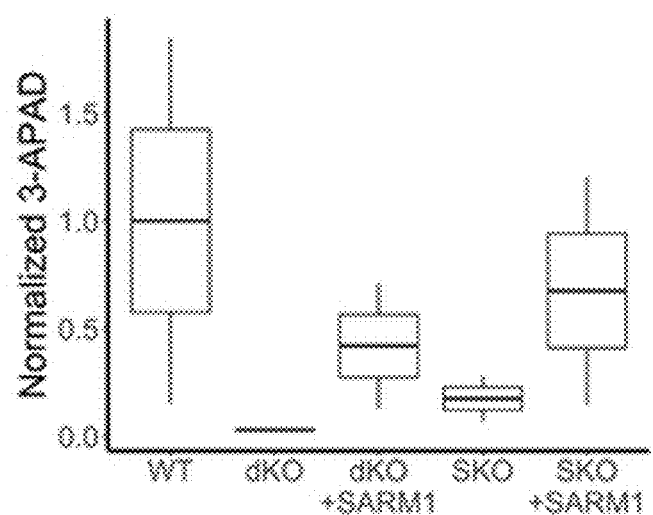

To determine whether this SARM1-mediated base exchange reaction occurs in neurons, the generation of 3-APAD was analyzed in neurons lacking the NAMPT/NMNAT pathway. Because Nmnat2 knockout mice are not viable, DRG neurons from Sarm1/Nmnat2 double-knockout (dKO) mice were used for these experiments. Sarm1/Nmnat2 dKO neurons treated with 3-AP do not produce 3-APAD. This demonstrates that 3-APAD production in cultured DRG neurons requires NMNAT2, but does not require its paralogs NMNAT1 or NMNAT3 (FIG. 3E). To further examine the import of the SARM1-mediated base exchange reaction, we infected Sarm1/Nmnat2 dKO neurons with lentivirus expressing SARM1 at DIV3 and examined metabolites at DIV7. Re-introducing SARM1 to these neurons restores 3-APAD production (FIG. 3E), demonstrating that SARM1 carries out the base exchange reaction in neurons. Indeed, Sarm1 KO neurons treated with 3-AP produce much less 3-APAD than do wild type neurons (FIG. 3E), indicating that SARM1 is a major contributor to 3-APAD synthesis. The residual 3-APAD produced in Sarm1 KO neurons treated with 3-AP demonstrates that the NAMPT/NMNAT pathway also actively produces 3-APAD from 3-AP. Together these results show that both SARM1-catalyzed base exchange activity and NAMPT/NMNAT2 contribute to 3-APAD synthesis in neurons.

Figure 4A:
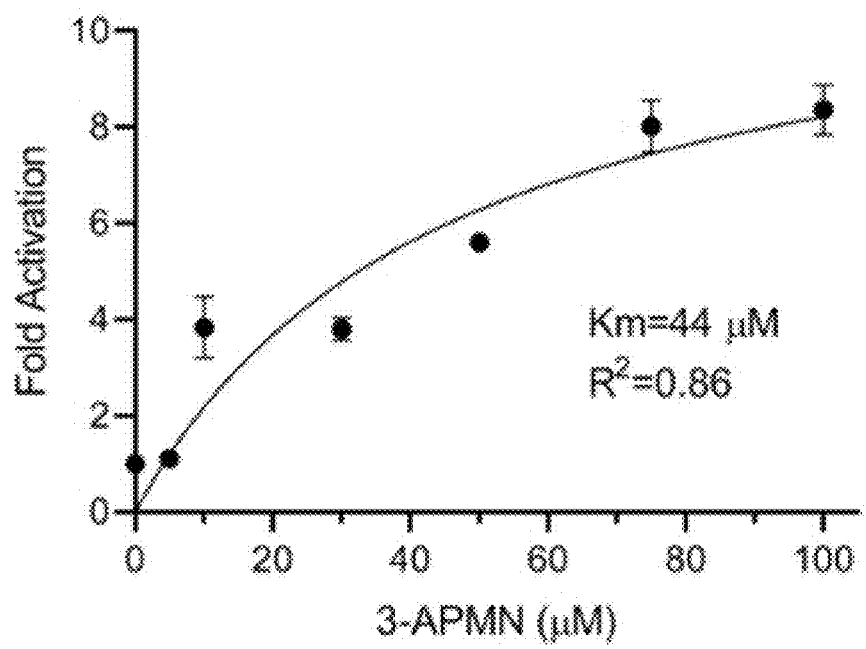
FIG. 4A-FIG. 4B show 3-APMN directly activates SARM1 via its allosteric binding site.

3-APMN activates purified SARM1 in vitro: The results from manipulating the NAMPT/NMNAT pathway and SARM1 in neurons support the hypothesis that 3-APMN can activate SARM1. To test whether SARM1 is directly activated by 3-APMN, SARM1 was purified on Strep-tag beads and incubated it with purified 3-APMN in the presence of the pyridine conjugate PC6, a fluorescent probe of SARM1 hydrolase activity. the reaction was measured in real time by following the fluorescence output signal and found that SARM1 hydrolase activity increases with 3-APMN concentration (FIG. 4A). The activation constant of the reaction (KA) was determined to be ~44 μM, which is slightly lower than the reported dissociation constant (KD) for $NAD^+$ binding to the SARM1 ARM domain. These results indicate that 3-APMN interacts directly with SARM1 to activate its $NAD^+$ hydrolase activity.

Figure 4B:
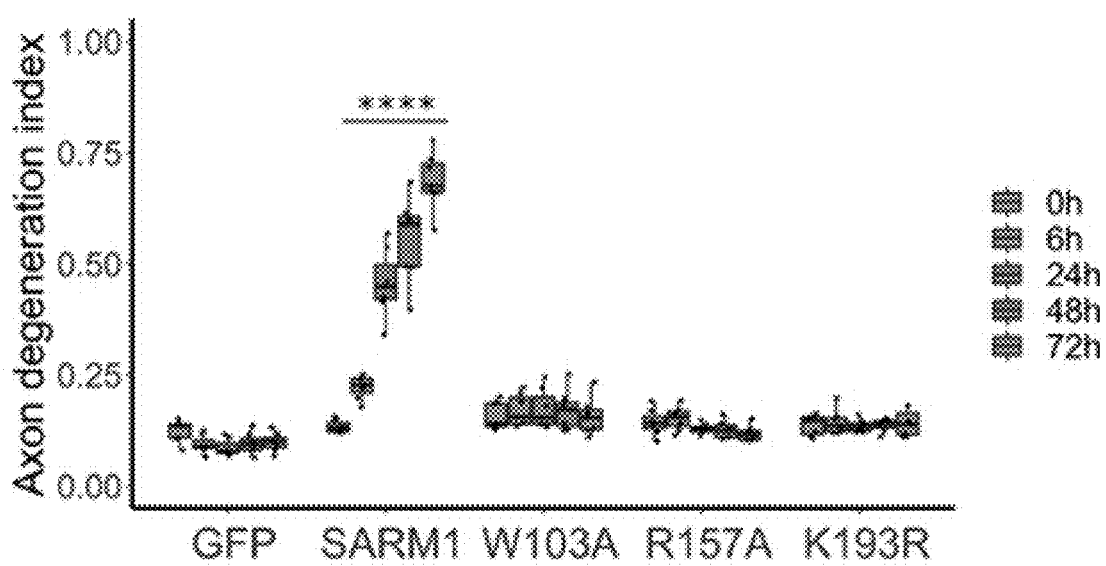

To determine whether 3-APMN activates SARM1 via the same binding pocket responsible for NMN-mediated SARM1 activation, several SARM1 mutants were examined in which this allosteric pocket is disrupted. SARM1 W103A, R157A and K193R were tested, three mutants in the allosteric pocket that are not activated in response to elevated NMN. Tellingly, lentiviral expression of wildtype SARM1 restores 3-AP-induced axon degeneration to Sarm1 KO DRG neurons, whereas the axons of 3-AP-treated neurons expressing any of the three SARM1 allosteric pocket mutants remain intact (FIG. 4B). Hence, the N-terminal allosteric site that binds NMN and $NAD^+$ is necessary for 3-AP-induced SARM1 activation.

Figure 5A:
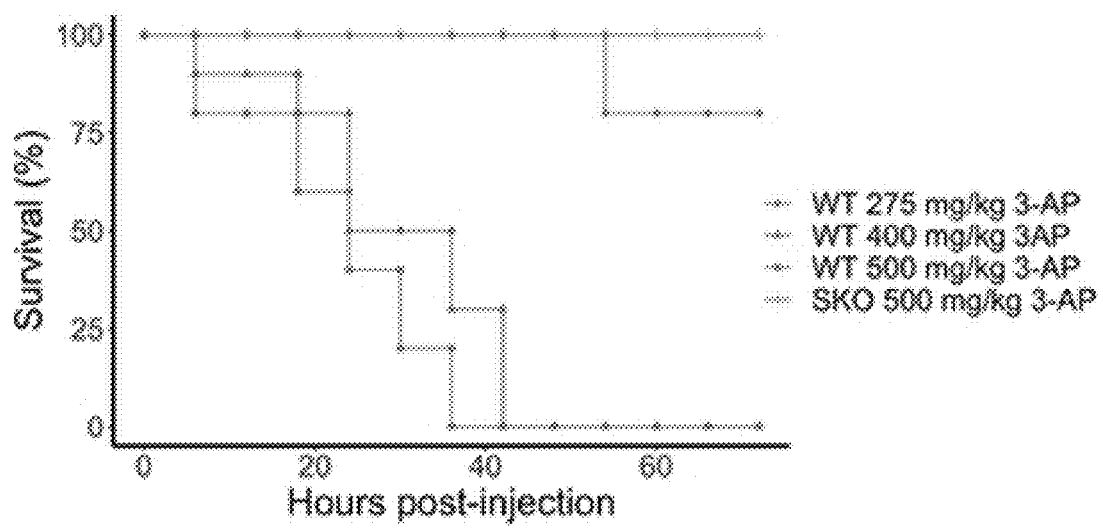
Figure 5B:
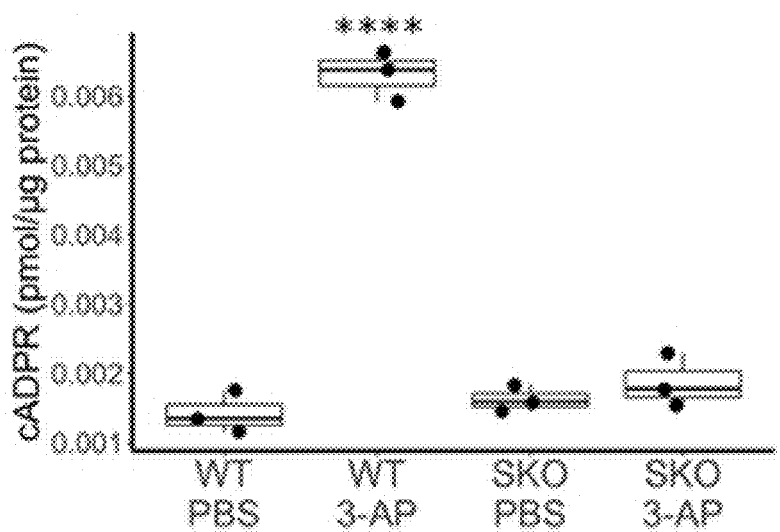

3-AP neurotoxicity in mice requires SARM1: Early animal experiments showed that intraperitoneal (IP) injection of 3-AP leads to rapid death accompanied by extensive lesions throughout the nervous system. To investigate the role of SARM1 activation in 3-AP toxicity in vivo, 3-AP was administered via IP injection to WT and Sarm1 KO mice. Wild type mice treated with 275 mg/kg 3-AP generally survive, but those treated with 400 mg/kg 3-AP die rapidly. In contrast, Sarm1 KO mice survive and have no obvious phenotype following treatment with up to 500 mg/kg 3-AP, a dose that is rapidly lethal for wild type mice (FIG. 5A). To assess SARM1 activation in vivo, levels of cADPR were monitored, a SARM1 biomarker. Following IP treatment with 275 mg/kg, levels of cADPR in the sciatic nerve increase 3-4 fold by 3 days post-administration (FIG. 5B). Similar injections into Sarm1 KO mice caused no alteration in cADPR levels, confirming the SARM1-dependence of cADPR production.

Figure 5C:
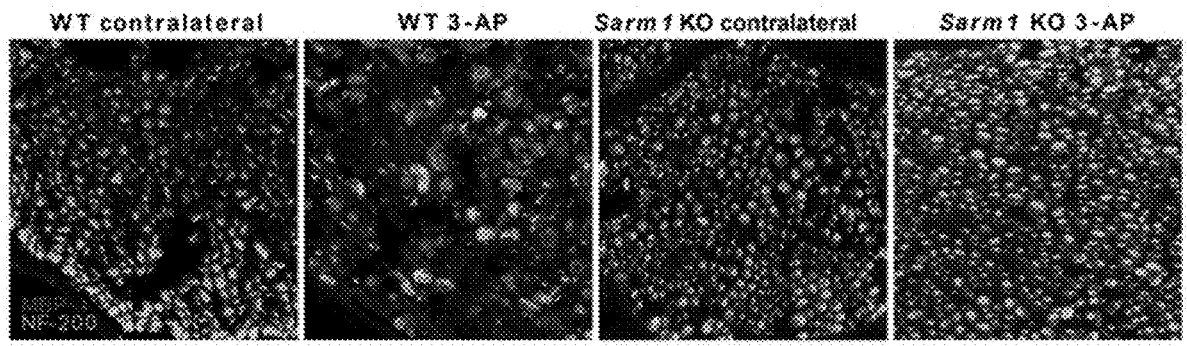
Figure 5D:
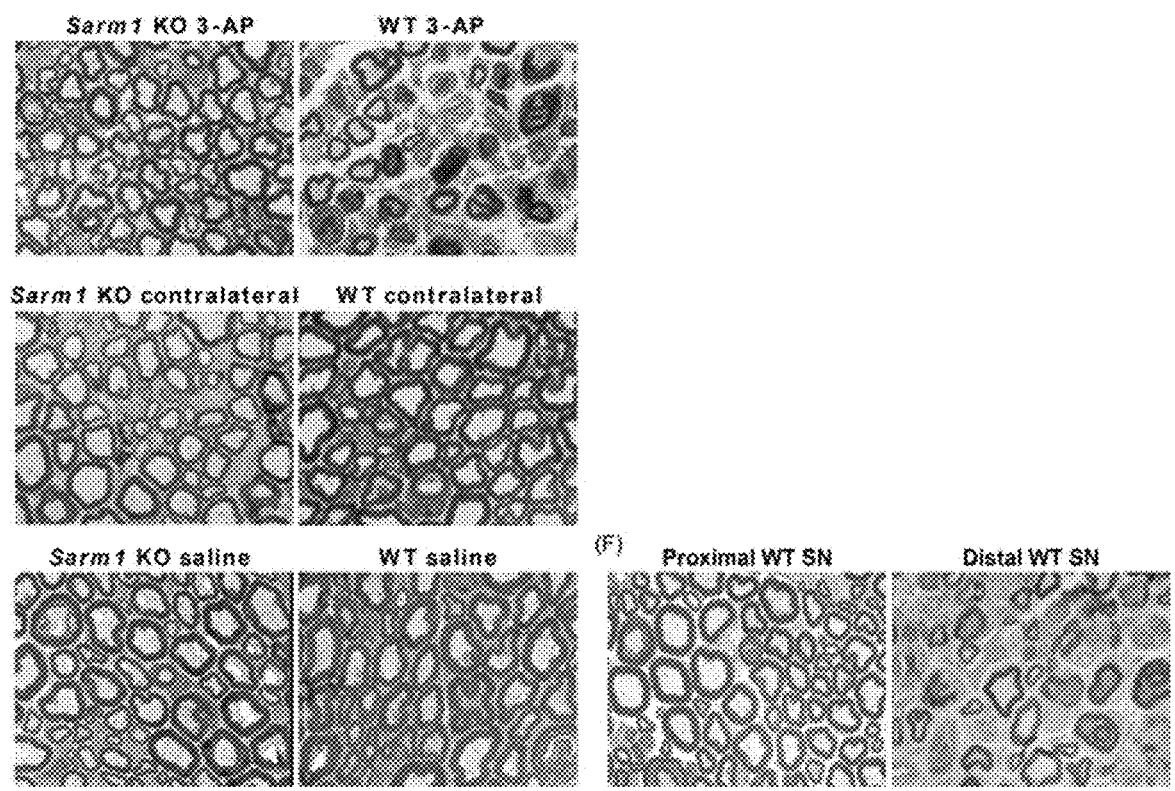
Figure 5E:
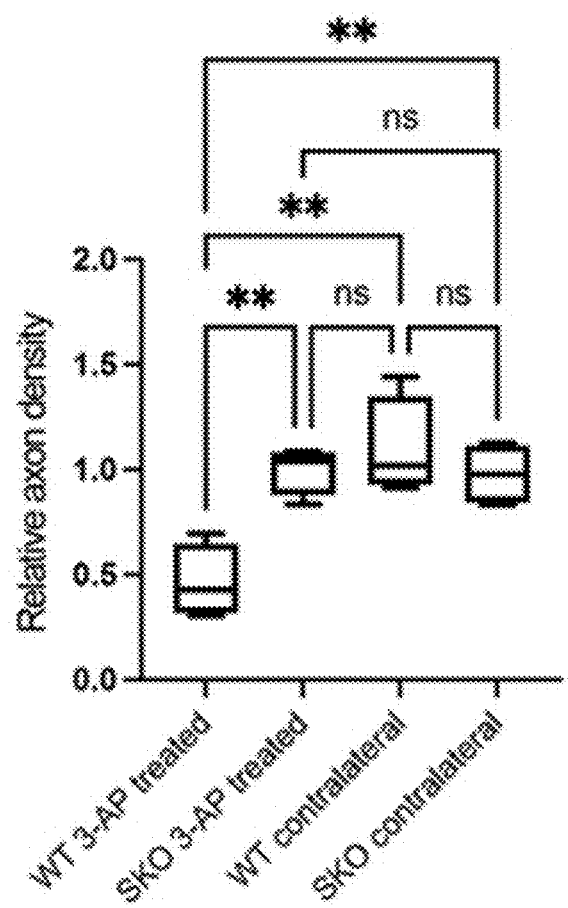

To examine the effect of 3-AP on axon degeneration and to circumvent systemic toxicity, we performed local administration by applying a Surgifoam wrap soaked in 500 mM 3-AP (or saline control) to surgically exposed sciatic nerve. After such treatment, WT mice rapidly develop an abnormal gait, favoring their untreated leg, and fail to splay the toes of their 3-AP treated paw in the usual fashion. Seven days after local treatment, the tibial nerves distal to the 3-AP treatment site were dissected and analyzed. 3-AP treated nerves from WT mice showed a dramatic loss of axons compared to the contralateral nerve or saline-treated nerve, demonstrating the local effect of 3-AP. In contrast to the findings in WT mice, treated nerves from Sarm1 KO mice were well protected from axon loss (FIG. 5C, FIG. 5D, and FIG. 5E). Quantification of axons in the tibial nerve shows a substantial axon loss in the 3-AP treated nerves (FIG. 5E). the sciatic nerve was also examined to explore whether degeneration proceeded retrograde to the site of 3-AP application. Axon degeneration only occurs distal to the site of application, with no detectable axon damage in the proximal sciatic nerve (FIG. 5F). The triggering of localized SARM1-dependent axon degeneration in vivo by restricted 3-AP application suggests that such a SARM1-activating neurotoxin is useful as a neurolytic agent.

Additional nicotinamide analogues induce SARM1-dependent axon degeneration: The pyridine ring is a common component of many drugs and industrial chemicals, suggesting that many of these compounds could also be neurotoxic in a SARM1-dependent fashion. To test whether other pyridine derivatives also bind and activate SARM1, 2-, 3-, and 4-aminopyridines and 2— 3-, and 4-acetylpyridines were tested in our axon degeneration and SARM1 activation assays. Interestingly, 2-aminopyridine causes axon degeneration in WT but not in Sarm1 KO neurons, similar to 3-AP, whereas the other related compounds failed to trigger axon degeneration even at very high doses (800 µM). Hence, multiple pyridine compounds exhibit SARM1-dependent toxicity, identifying SARM1 as a candidate target for the many toxins with related chemical structures.

Figure 6:
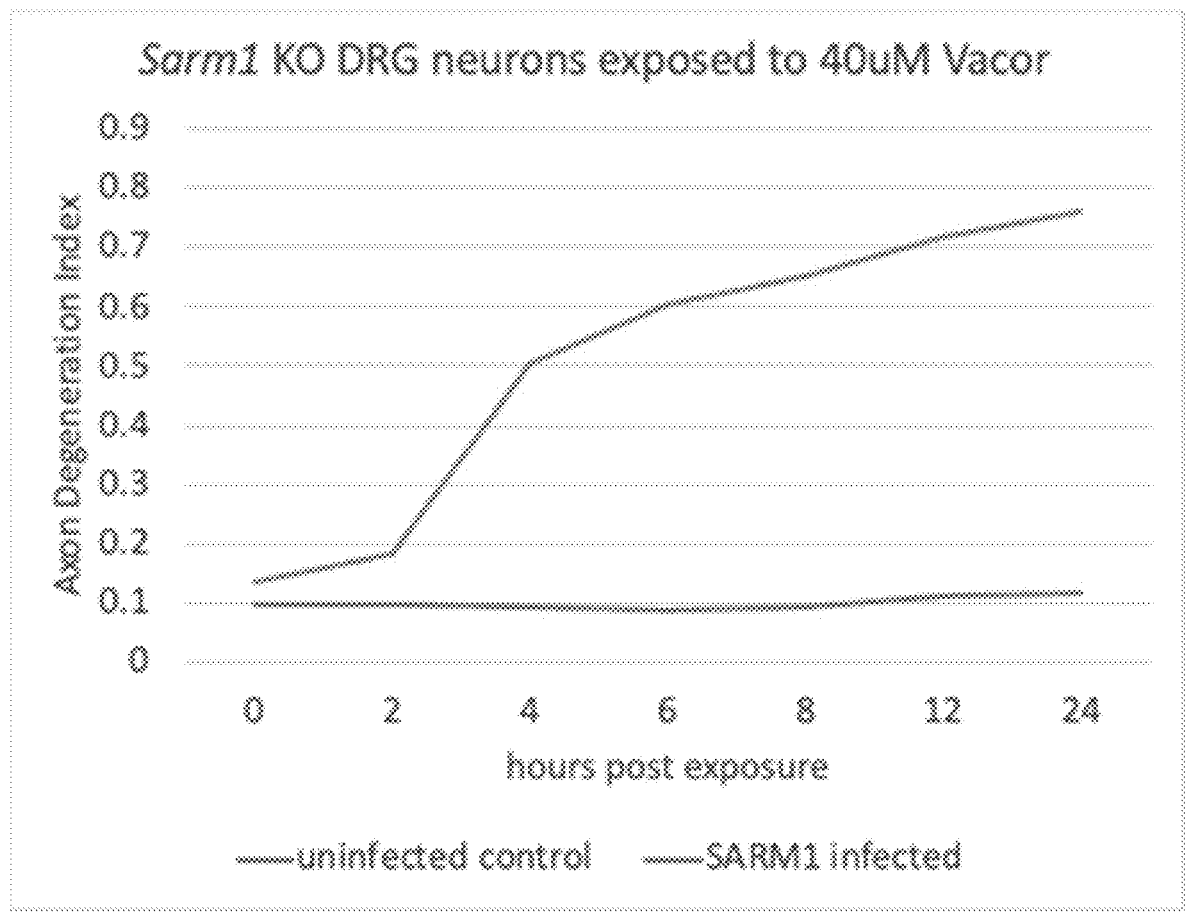
FIG. 6 shows treatment of sensory neurons with vacor triggers SARM1-dependent axon degeneration.
Figure 7:
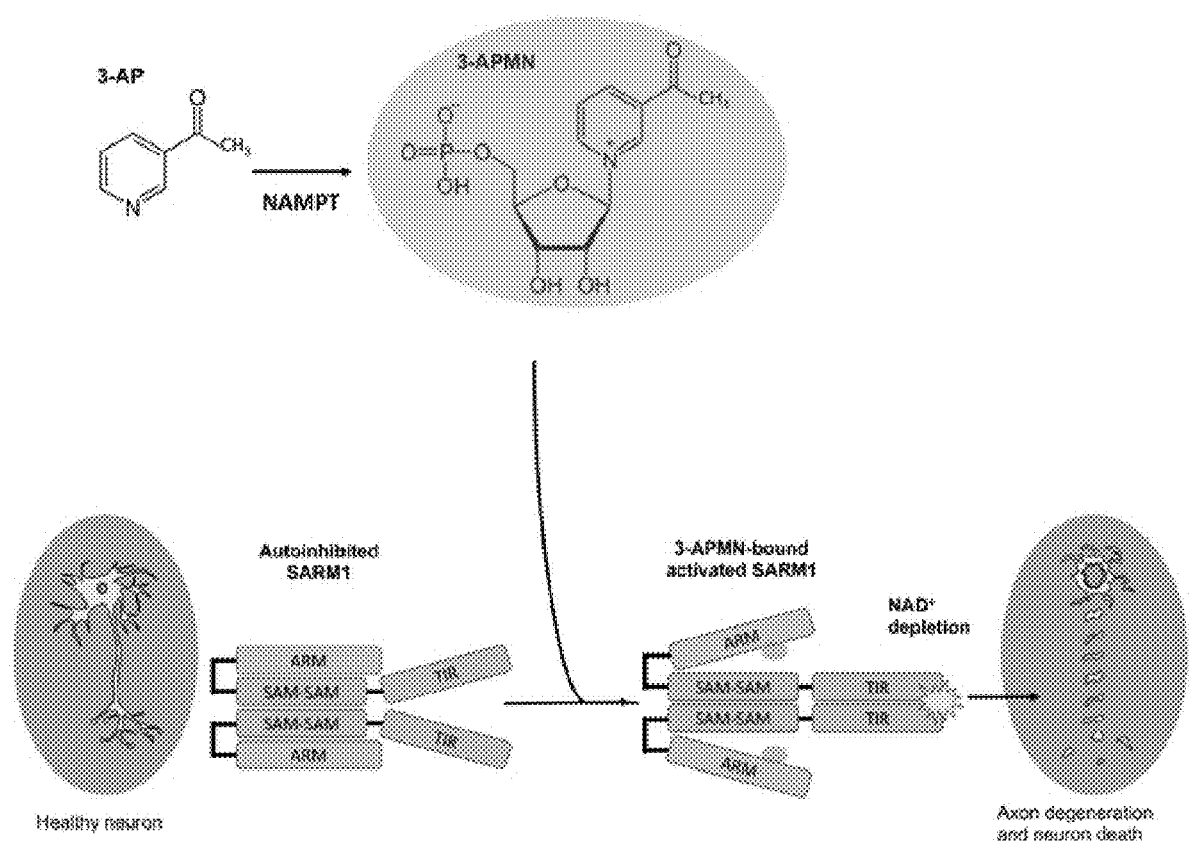
FIG. 7 shows an exemplary embodiment of the disclosure where 3-AP is converted to 3-APMN to activate SARM1 mediated targeted axon degeneration.

Indeed, a further nicotinamide derivative included among these SARM1 activator prodrugs is Pyrinuron (N-(4-Nitrophenyl)-N'-[(pyridin-3-yl)methyl]urea) a.k.a. Vacor, a powerful neurotoxin formerly employed as a rodenticide. Like nicotinamide and 3-AP, Vacor is an NAMPT substrate metabolized to form an NMN analog, Vacor mononucleotide (VMN). Neuron degeneration induced by Vacor was also shown to be SARM1-dependent (FIG. 6) and, notably, local application of Vacor to neurites causes distal neurite degeneration without harming neuron cell bodies.

Discussion

A major advance in the understanding of programmed axon degeneration was the recent discovery that SARM1, the central axon executioner, is activated by a rise in the intracellular ratio of the nicotinamide metabolites NMN to $NAD^+$. The present example expands on this breakthrough to expose the mechanism of a decades-old biological riddle, the dramatic neurotoxicity of 3-AP and related compounds. These results support a model in which 3-AP is metabolized to produce the NMN mimetic 3-APMN which binds the allosteric pocket of SARM1, thereby activating its NADase activity and initiating pathological axon degeneration. The identification of SARM1 as a direct target of neurotoxins has two important implications. First, these findings suggest that SARM1 activation by environmental toxins is a potential contributor to neurodegenerative disorders. Second, the identification of selective SARM1 agonists are useful in new approaches for therapeutic neurolysis.

The nervous system employs an active program of axon self-destruction, also known as Wallerian degeneration, to facilitate the orderly clearance of axon segments damaged by trauma or disease. The choice between axon maintenance and dissolution is chiefly made by the TIR-containing $NAD^+$ hydrolase SARM1. Healthy neurons maintain SARM1 in an autoinhibited state, but injury- or disease-associated attrition of the $NAD^+$ synthetase NMNAT2 induces rapid $NAD^+$ depletion by SARM1 leading to metabolic catastrophe and axon fragmentation. Thus $NAD^+$ homeostasis is crucial for axon maintenance as well as overall neuronal health. $NAD^+$ is generated from Nam in two steps: the rate-limiting conversion of Nam to NMN by NAMPT, followed by synthesis of $NAD^+$ from NMN by NMNAT2 and its paralogs. NMN and $NAD^+$ compete to bind an allosteric pocket that modulates SARM1 autoinhibition, rendering SARM1 a metabolic sensor that responds to an elevated NMN/$NAD^+$ ratio. As such, experimental manipulations that alter the apparent concentration of either metabolite, whether by short-circuiting the usual synthesis pathway or by interjecting an NMN mimetic, directly affect SARM1 activity and its consequences.

It was first observed three quarters of a century ago that treatment with a nicotinamide analog, 3-AP, induces rapid hindlimb paralysis and death in mice, symptoms that could be prevented by sufficient prior fortification with nicotinic acid or Nam. 3-AP-treated animals develop widespread nervous system lesions, particularly in brainstem nuclei, and consecutive treatment with 3-AP and Nam was eventually developed into a useful method for specific ablation of the inferior olive in rodents. However, the mechanism of 3-AP neurotoxicity remained unknown. The present example provides comprehensive evidence demonstrating that 3-AP injures the nervous system by directly activating SARM1 and inducing Wallerian degeneration.

The profound invulnerability of both Sarm1−/− mice and Sarm1−/− cultured neurons to 3-AP first alerted us to the SARM1-dependence of 3-AP toxicity and lead to the straightforward hypothesis that 3-APMN, a 3-AP metabolite nearly identical to NMN, hijacks the SARM1 pathway by binding the enzyme's allosteric site and triggering its pro-degenerative activity. Analysis of 3-AP-treated wildtype neurons confirmed the presence of 3-APMN and its derivative 3-APAD, as well as the specific SARM1 activity marker, cADPR. The present example provided two further key pieces of evidence: 1) the demonstration that 3-APMN directly binds and activates SARM1, and 2) that manipulating 3-APMN levels in 3-AP-exposed neurons correspondingly alters SARM1 activity and its toxic consequences. Both of these criteria were demonstrated using both in vitro and in vivo methods, elucidating the mechanism of action of this long-studied neurotoxin. Moreover, this proposed mechanism of SARM1-dependent 3-AP toxicity surely applies to other structural-similar pyridine derivatives, and 2-aminopyridine was identified as such a case. Thus, SARM1 activation may be a common cause of neurotoxicity caused by pyridine compounds.

In the course of demonstrating the SARM1-dependence of 3-AP toxicity in vivo, peripheral nerves were exposed to 3-AP in order to determine whether the toxin could stimulate localized neurodegeneration. Prior in vivo studies of 3-AP were confined to systemic administration. A key motivation for these experiments was to explore the potential utility of 3-AP or other pyridines for therapeutic neurolysis—the application of physical or chemical agents to effect temporary degeneration of nerves distal to a targeted lesion. Purposeful nerve destruction can be appropriate for a variety of severe pain conditions, especially visceral pain associated with pancreatic cancer, trigeminal neuralgia, or facetogenic and vertebral pain. Gratifyingly, it was found that local application of 3-AP caused rapid degeneration of the exposed nerve fibers without apparent systemic harm. Further, the 3-AP injury signaling did not progress anterogradely, thus sparing the proximal nerve. Currently, chemical neurolysis is achieved by injecting phenol or ethanol, nonspecific noxious agents that can damage non-neuronal tissues. While both chemicals are highly efficacious, ethanol injection produces severe burning pain and phenol may cause systemic complications such as nausea, cardiovascular depression and cardiac arrhythmias. Therefore, a neuroselective agent could expand the option of neurolysis beyond its current limited indications to more broadly treat neuropathic pain. Because neurolytic techniques specifically exploit Wallerian degeneration to ablate axons, a SARM1 agonist fits well with this application. Thus, in the best traditions of medicine, the solution to a toxicological mystery may be adapted into a useful therapeutic.

Methods

Mice: All experiments were performed in accordance with the protocols of the Institutional Animal Care and Use Committee of Washington University in St. Louis and the guidelines for the Care and Use of Laboratory Animals of the National Institutes of Health. Mice were housed on a 12 hr light dark cycle with less than 5 mice per cage and with water and food available at all times. Male and female mice were used for all experiments. 5-week old mice were used for IP injection and 5-6-month old mice were used for Surgifoam wrap treatments. Sarm1 KO mice were a gift from Macro Colonna at Department of Pathology and Immunology, Washington University School of Medicine in St. Louis, and C57BL/6 mice were purchased from Jackson Laboratory.

Mammalian cell lines: HEK 293T cells (ATCC) and HEK 293T cells stably-expressing Nicotinamide Riboside Kinase 1 (NRK1) were cultured in Dulbecco's Modified Eagle Medium (DMEM) (Thermofisher Scientific) supplemented with 10% FBS, penicillin/streptomycin and glutamine. Both cell lines were cultured in a 37° C. incubator with 5% $CO_2$. Cells were passed every 3-4 days using 0.05% Trypsin containing 0.02% EDTA (Gibco).

Bacterial cultures: StrepTag-NAMPT and StrepTag-NMNAT1 were cloned into pET30a+ plasmids. Plasmids were transformed into T7 Express Competent E. coli (New England BioLabs) as described previously. Single colonies were selected and grown overnight at 37° C. Cultures were diluted in LB media, IPTG (1 mM) was added at A600=0.6, and bacteria were induced for another 4 hr before harvest. See 'NAMPT and NMNAT1 production in E. coli' section for subsequent protein purification.

DRG neuron culture: Mouse DRG culture was as described previously. Mouse DRGs were dissected at embryonic day 13.5. Approximately 50 ganglia were collected from each embryo and dissociated in 0.05% Trypsin containing 0.02% EDTA (Gibco) at 37° C. for 20 min. The DRG neurons were washed 3 times with DRG culture medium after incubation with Trypsin. Cells were seeded as spot cultures in 96-tissue culture plates (Corning) coated with 0.1 mg/ml poly-D-lysine and 0.1 mg/ml laminin. They were cultured in Neurobasal (Gibco) containing 2% B27 (Invitrogen), 100 ng/ml 2.5S NGF (Harlan Bioproducts), and 1 µM 5-fluoro-2'-deoxyuridine/1 µM uridine. The culture medium was exchanged with fresh DRG culture medium every 2-3 days. Lentiviruses were added 3 days after seeding (DIV3).

Lentivirus production: Lentivirus production was performed as described previously. HEK 293T cells were seeded with the density of $1 \times 10^6$ in 35 mm well tissue culture plate (Corning). Transfection was performed one day after seeding the cells. Lentiviral constructs were co-transfected with VSV-G and psPAX2 lentiviral packing vectors. Two days after transfection, lentiviruses were collected from culture supernatant and concentrated with Lenti-X concentrator (Clontech). Lentiviruses were suspended in ¹⁄₁₀ volume of culture supernatant with PBS, and stored at −80° C.

Quantification of axon degeneration: After culture for 7 days, axotomy was performed by cutting DRG axons manually with a razor blade. After axon transection, bright-field images of distal axons were taken using the Operetta automated imaging system (PerkinElmer). Axon degeneration indexes were calculated from these bright-field images using ImageJ (NIH). The axon degeneration index was calculated as the ratio of fragmented axon areas as previously described. Indexes were calculated as the average of six fields per well.

NAMPT and NMNAT1 production in E. coli: Protein purification was performed using StrepTactin Megbeads (Cube Biotech). The beads were washed with HEPES buffer (50 mM HEPES/NaOH pH 7.5, 300 mM sodium chloride, 20% glycerol with EDTA-free protease inhibitors) and proteins were eluted with 5 mM dethiobiotin (50 mM HEPES/NaOH pH 7.5, 300 mM sodium chloride, 20% glycerol, 5 mM dethiobiotin with EDTA-free protease inhibitors). Protein concentrations were determined by Pierce™ BCA Protein Assay (Thermofisher Scientific).

SARM1 protein purification from mammalian cells: A HEK 293T cell line stably expressing NRK1 was used to produce SARM1 protein as previously described. In short, plasmid containing N-terminal StrepTag-SARM1 was transfected into NRK1-HEK 293T cells using X-tremeGENE reagent (Millipore Sigma). After 2 days, the cells were harvested and re-suspended with binding buffer (100 mM Tris-HCL pH 8, 150 mM sodium chloride, 0.01% Tween-20 with EDTA-free protease inhibitors (Pierce)). After sonication, cell debris was removed by centrifugation at 15,000×g for 10 minutes. Soluble lysates were then mixed with StrepTactin Megbeads (Cube Biotech) equilibrated with the same binding buffer. After incubation at 4° C. for 60 minutes, beads were washed with washing buffer (25 mM HEPES, pH 7.5 and 150 mM NaCl with EDTA-free protease inhibitors). If elution was not required, SARM1 containing beads were re-suspended in washing buffer with addition of 1 mM TCEP and stored at −80° C. before further use.

Base exchange assay and metabolite extraction for HPLC and LC-MS/MS: SARM1 protein was eluted from the beads by incubating for 15 min at 4° C. degree in eluting buffer (25 mM HEPES/NaOH pH 7.5, 150 mM sodium chloride, 20% glycerol, 5 mM desthiobiotin with EDTA-free protease inhibitors). In a typical assay, 500 ng SARM1 protein was mixed with 50 µM or 100 µM NAD$^+$ and ascending concentrations of 3-AP (20 µM, 40 µM, 60 µM). The reactions were incubated at 37° C. degree for 1 hr in a total reaction volume of 50 µl. For HPLC analysis, the reaction was stopped by addition of 50 µl 0.5 M perchloric acid (HClO4) and then neutralized with 3 M potassium carbonate ($K_2CO_3$). After neuralization and removal of precipitate by centrifugation, 50 µl supernatant was loaded onto HPLC. For LC-MS/MS analysis, the reaction was stopped by addition of 50 µl 50% methanol and metabolites were extracted using ⅓ total volume of chloroform. The aqueous phase was lyophilized and stored at −20° C. for LC-MS/MS analysis.

3-APMN identification by LC-MS/MS and purification by FPLC: Reactions were carried out using 5 µg NAMPT enzyme, 500 µM 3-AP, 1 mM ATP, 500 µM PRPP in HEPES buffer (50 mM HEPES pH 7.5, 20 mM $MgCl_2$) and incubated for 6 hr at 37° C. Reactions with or without PRPP (obligate cofactor) were stopped by addition of equal volume of 50% methanol and metabolites were extracted using chloroform. The lyophilized aqueous phase was analyzed by LC-MS/MS to identify 3-APMN. 3-APAD was identified similarly from reactions containing both NAMPT and NMNAT1 using LC-MS/MS. After HPLC separation, 3-APMN was purified through FPLC. In short, an ion-exchange chromatography (IEC) was carried out on AKTA Purifier (GE HealthCare) using an anion exchange column Source 15Q 4.6/100 PE (GE HealthCare). The column was equilibrated with 0.01 M ammonium acetate, pH 9.0 at room temperature with a flow rate of 1 ml/min. After injection of the reaction mixture, a linear gradient elution was applied by mixing the 0.01 M and 1 M ammonium acetate, pH 9.0 buffers at 1 ml/min. The eluate was monitored at wavelength 260 nm. Peaks were collected and lyophilized. Next, lyophilized samples were reconstituted with 5 mM ammonium formate and the identity of 3-APMN peak was confirmed using LC-MS/MS (Agilent, 6470 Triple Quad LC/MS) with a C18 column (Agilent, EclipsePlus C18, 3.0×50 mm, 1.8 mm particles).

SARM1 activation assay by PC6 fluorescence: Modified from previous paper, typically, in a mixture of 50 µl, ~200 ng of SARM1(on-beads) was mixed with 50 µM PC6, 50 µM NAD$^+$ and 0 to 100 µM of purified 3APMN. The reaction was carried out in a Bio Tek's Cytation 5 plate reader at 25° C. Fluorescence signal, which corresponds to PAD6 formation, was recorded with 405 nm excitation and 520 nm emission wavelengths every 2 minutes. The production rate of PAD6 was calculated based on the fluorescence changes within the first 30 minutes of reaction.

Metabolite measurement using LC-MS/MS: Lyophilized samples were reconstituted with 50 µl of 5 mM ammonium formate and centrifuged at 12,000 g for 10 min. Cleared supernatants were transferred to sample vials. Serial dilutions of standards for each metabolite in 5 mM ammonium formate were used for calibration. HPLC-mass spectrometry analysis was performed on an Agilent 1290 Infinity II liquid chromatography system (Agilent Technologies, Santa Clara, CA) with a flexible pump, multisampler, sample cooler and an MCT containing an Atlantis T3 column (2.1×150 mm, 3 µm) and VanGuard guard cartridge (2.1 mm×5 mm, 3 µm) (Waters, Milford, MA), coupled to an Agilent 6470 Triple Quad mass spectrometer (Agilent Technologies, Santa Clara, CA). The mobile phase (0.15 ml/min) was 5 mM ammonium formate in water (A) and 100% methanol (B). The column was equilibrated with 0% B, maintained after injection for 2 min, then a linear gradient to 20% B applied over 4 min. The column was then ramped to 50% B over 2 min, and held at 50% for 2 min, then reverted back to 0% B over the next 5 min and allowed to re-equilibrate at 0% B for 9 min. The total run time was 24 min per sample. The injection volume was 10 µl. The mass spectrometer was equipped with an electrospray ion source which was operated in positive ion multiple reaction monitoring (MRM) mode for the detection of all of the metabolites. The [M+H]+ transitions were optimized for each metabolite and were selected as follows: m/z 664→428 for NAD$^+$, m/z 335→123 for NMN, m/z 542→428 for cADPR, m/z 508→136 for ATP, m/z 663→136 for 3-APAD and m/z 334→122 for 3-APMN. The mass spectrometer settings for the fragmentation, the collision energy (CE) and the cell accelerator voltage were optimized for each of these transitions. Raw data were acquired and quantified using MassHunter Workstation software version B.08.00 for 6400 Series Triple Quadrupole (Agilent Technologies, Santa Clara, CA).

IP injection and local application of 3-AP to sciatic nerve using Surgifoam wrap 5 week-old mice were used for IP injection experiment. Suitable skin incisions were made at the mid-thigh level of 5 week-old mice, followed by a small incision or blunt dissection to the muscle fascia to permit retraction of the biceps femoris and gluteus superficialis muscles to expose the sciatic nerve. The nerve was carefully separated from surrounding connective tissue and then a 0.5×1 cm piece of sterile absorbable hemostatic material (Surgifoam) soaked in 500 mM 3-AP (or saline control) was wrapped around the sciatic nerve. Wound clips, and/or tissue adhesive were used to close the incision.

Tissue processing: Tibial nerves from both control and 3-AP treated sides was dissected out 7 days post-surgery. The distal 2 cm portion of the nerve was fixed in 4% paraformaldehyde for 1 hr at room temperature, then moved to 30% sucrose and embedded in OCT for cryosectioning in the following day. Immunocytochemistry was performed on tibial cryosections using NF200 (Sigma N4142, 1:1000) and MBP (Millipore MAB386, 1:100) followed by anti-rabbit-Alexa488 (1:500) and anti-rat-Cy3 (1:500). The proximal 2 cm portion of the sciatic nerves were fixed in 3% Glutaraldehyde for processing and embedding in epoxy/plastic. Toluidine blue thick sections (400-600 nm thickness) were cut and axon counting was performed using binary image analysis.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs); and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is a fish or reptile.

The term "administer," "administering," or "administration" refers to implanting, absorbing, ingesting, injecting, inhaling, or otherwise introducing a compound or cell described herein or generated as described herein, or a composition thereof, in or on a subject.

The terms "treatment," "treat," and "treating" refer to reversing, alleviating, delaying the onset of, or inhibiting the progress of a disease. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen and/or in light of detecting that the subject has a genotype associated with the disease). Treatment may also be continued after symptoms have resolved, for example, to delay or prevent recurrence.

The terms "condition," "disease," and "disorder" are used interchangeably.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for treating pain in a subject in need thereof, comprising: locally administering a composition comprising 10 μM to 50 μM of a SARM1 activating agent at the site of the pain, wherein the SARM1 activating agent is Vacor; Vacor-mononucleotide (VMN); or a prodrug thereof.

2. The method of claim 1, wherein the SARM1 activating agent does not cause systemic effects and/or does not damage non-neural tissues adjacent to a targeted nerve.

3. The method of claim 1, wherein the subject has or is suspected of having a disease, disorder, or condition where degeneration of motor neurons is therapeutic or beneficial.

4. The method of claim 1, wherein the subject has or is suspected of having a pain condition.

5. The method of claim 4, wherein the pain condition is post-amputation pain, post-injury pain, post-surgical pain, post-traumatic pain, or neuropathic pain.

6. The method of claim 4, wherein the pain condition is neuroma pain.

7. The method of claim 1, wherein the subject has or is suspected of having neuroma, an inappropriate growth of sensory axons after injury or surgery.

8. The method of claim 7, wherein the SARM1 activator applied to a neuroma selectively triggers the degeneration of the neuroma.

9. The method of claim 3, wherein the subject has or is suspected of having a muscle contraction disease, disorder, or condition.

10. The method of claim 9, wherein the motor disease disorder, or condition or muscle contraction disease disorder, or condition is selected from one or more of:
neck spasms (cervical dystonia),
excessive sweating (hyperhidrosis),
an overactive bladder,
lazy eye,
facial wrinkles,
migraines,
muscle contractures,
cerebral palsy,
bladder dysfunction, or
eye twitching.

11. The method of claim 3, wherein the subject has or is suspected of having a cosmetic defect, facial paralysis, facial palsy, synkinesis, hypertonicity of the buccinator muscle, hemifacial spasm, facial wrinkles, neck spasms, excessive sweating, an overactive bladder, lazy eye, eye twitching, or chronic migraines.

12. The method of claim 1, wherein the SARM1 activating agent is metabolized intracellularly to generate a SARM1 active metabolite.

13. The method of claim 1, wherein the SARM1 activating agent is Vacor.

* * * * *